United States Patent
Yu et al.

(10) Patent No.: US 10,682,392 B2
(45) Date of Patent: Jun. 16, 2020

(54) METHODS FOR TREATING PULMONARY HYPERTENSION WITH A TGF-BETA TYPE II RECEPTOR-FC FUSION PROTEIN

(71) Applicants: THE BRIGHAM AND WOMEN'S HOSPITAL, INC., Boston, MA (US); ACCELERON PHARMA, INC., Cambridge, MA (US)

(72) Inventors: Paul Yu, Boston, MA (US); Asya Grinberg, Lexington, MA (US); Dianne S. Sako, Medford, MA (US); Roselyne Castonguay, Malden, MA (US); Rita Steeves, Stoneham, MA (US); Ravindra Kumar, Acton, MA (US)

(73) Assignees: THE BRINGHAM AND WOMEN'S HOSPITAL, INC., Boston, MA (US); ACCELERON PHARMA, INC., Cambridge, MA (US)

(*) Notice: Subject to any disclaimer, the term of this patent is extended or adjusted under 35 U.S.C. 154(b) by 0 days.

(21) Appl. No.: 15/037,852

(22) PCT Filed: Nov. 21, 2014

(86) PCT No.: PCT/US2014/066776
§ 371 (c)(1),
(2) Date: May 19, 2016

(87) PCT Pub. No.: WO2015/077540
PCT Pub. Date: May 28, 2015

(65) Prior Publication Data
US 2016/0287664 A1 Oct. 6, 2016

Related U.S. Application Data

(60) Provisional application No. 61/907,260, filed on Nov. 21, 2013.

(51) Int. Cl.
| | | |
|---|---|---|
| A61P 9/12 | (2006.01) | |
| A61K 38/17 | (2006.01) | |
| C07K 14/71 | (2006.01) | |
| C07K 14/705 | (2006.01) | |
| C07K 19/00 | (2006.01) | |

(52) U.S. Cl.
CPC ............ *A61K 38/179* (2013.01); *A61P 9/12* (2018.01); *C07K 14/71* (2013.01); *C07K 19/00* (2013.01); *C07K 2319/30* (2013.01)

(58) Field of Classification Search
None
See application file for complete search history.

(56) References Cited

U.S. PATENT DOCUMENTS

| | | | |
|---|---|---|---|
| 6,294,350 B1 | 9/2001 | Peterson | |
| 9,809,637 B2 | 11/2017 | Kumar et al. | |
| 9,884,900 B2 | 2/2018 | Kumar et al. | |
| 2005/0203022 A1* | 9/2005 | Gotwals | C07K 14/71 435/69.1 |
| 2005/0230022 A1* | 10/2005 | Guerinon | B60C 15/0018 152/543 |
| 2007/0014767 A1 | 1/2007 | Ezquerro Saenz et al. | |
| 2007/0077598 A1 | 4/2007 | Breit et al. | |
| 2009/0186016 A1 | 7/2009 | Rade et al. | |
| 2010/0003256 A1 | 1/2010 | Sheppard et al. | |
| 2011/0172296 A1 | 7/2011 | Bennett et al. | |
| 2011/0236309 A1 | 9/2011 | O'Connor-McCourt et al. | |
| 2011/0319406 A1 | 12/2011 | Kim et al. | |
| 2013/0287688 A1 | 10/2013 | Jain et al. | |
| 2015/0056199 A1 | 2/2015 | Kumar et al. | |
| 2016/0376341 A1* | 12/2016 | Kumar | C07K 14/71 424/134.1 |

FOREIGN PATENT DOCUMENTS

| | | |
|---|---|---|
| EP | 0975771 B1 | 7/2007 |
| WO | 98/48024 A1 | 10/1998 |
| WO | 99/65948 A1 | 12/1999 |
| WO | 2009/026204 A1 | 2/2009 |
| WO | 2012/093125 A1 | 7/2012 |
| WO | 2012/145539 A1 | 10/2012 |

(Continued)

OTHER PUBLICATIONS

Megalou et al (Oct.-Dec. 2012. Pulmonary Circulation. 2(4): 461-469).*
Megalou et al., "Transforming growth factor-β inhibition attenuates pulmonary arterial hyerptension in rats", International Journal of Clinical and Experimental Medicine 3(4):332-340 (2010).
Rabbani et al., "Soluble TGFβ Type II Receptor Gene Therapy Ameliorates Acute Radiation-Induced Pulmonary Injury in Rats", International Journal of Radiation Oncology* Biology* Physics 57(2):563-572 (2003).
Yung et al., "Abstract 17285: A Selective Transforming Growth Factor-β and Growth Differentiation Factor-15 Ligand Trap Attenuates Pulmonary Hypertension", Circulation 130:A17285 (2014). (4 pages).

(Continued)

*Primary Examiner* — Zachary C Howard
(74) *Attorney, Agent, or Firm* — Nixon Peabody LLP; David S. Resnick; Ravinderjit Braich

(57) ABSTRACT

In some aspects, the invention teaches pharmaceutical compositions that include a TGF-beta ligand trap, and methods of using a TGF-beta ligand trap to treat, prevent, or reduce the progression rate of pulmonary hypertension (PH). The invention also provides methods of using a TGF-beta ligand trap to treat, prevent, or reduce the progression rate of a variety of conditions including, but not limited to, pulmonary vascular remodeling, pulmonary fibrosis, right ventricular hypertrophy, diseases associated with excessive TGF-beta signaling, diseases associated with excessive GDF15 signaling, and diseases associated with excessive PAI-1 signaling. The invention further provides methods of using a TGF-beta ligand trap to reduce right ventricular systolic pressure in a subject.

11 Claims, 11 Drawing Sheets
Specification includes a Sequence Listing.

(56) References Cited

FOREIGN PATENT DOCUMENTS

| WO | 2013/019805 A1 | 2/2013 |
|---|---|---|
| WO | 2013/059879 A1 | 5/2013 |
| WO | 2015/027082 A1 | 2/2015 |
| WO | 2015/179227 A1 | 11/2015 |
| WO | 2015/189790 A1 | 12/2015 |
| WO | 2016/019368 A1 | 2/2016 |

OTHER PUBLICATIONS

Yung et al., "A Selective Transforming Growth Factor-β Ligand Trap Attenuates Pulmonary Hypertension", American Journal of Respiratory and Critical Care Medicine 194(9):1140-1151 (2016).
Meadows et al., "Increased expression of growth differentiation factor-15 in systemic sclerosis-associated pulmonary arterial hypertension", Chest, 139(5):994-1002 (2010).
Gonzalez-Nunez et al., "The ALK-1/SMAD1 pathway in cardiovascular physipathology: a new target for therapy?", Biochem Biophys Acta, 1832(10):1492-1510 (2013).
Czajkowsky et al., "Fc-fusion proteins: new developments and future perspectives", EMBO Mol Med. 4(10):1015-1028 (2012).
Rainer et al., "Cardiomyocyte-Specific Transforming Growth Factor β Suppression Blocks Neutrophil Infiltration, Augments Multiple Cytoprotective Cascades, and Reduces Early Mortality After Myocardial Infarction", Circulation Research 114:1246-1257 (2014).
Samuel et al., "Serelaxin is a More Efficacious Antifibrotic Than Enalapril in an Experimental Model of Heart Disease", Hypertension 64:315-322 (2014).
Akhurst et al., "Targeting the TGFβ signalling pathway in disease", Nature Reviews Drug Discovery 11(10):790-811 (2012).
Aschner et al., "Transforming Growth Factor-β: Master Regulator of the Respiratory System in Health and Disease", American Journal of Respiratory Cell and Molecular Biology 54(5):647-655 (2016).
Botney et al., "Vascular Remodeling in Primary Pulmonary Hypertension: Potential Role for Transforming Growth Factor-β", American Journal of Pathology 144(2):285-295 (1994).
Chen et al., "Dominant negative mutation of the TGF-β receptor blocks hypoxia-induced pulmonary vascular remodeling", Journal of Applied Physiology 100:564-571 (2006).
Derrett-Smith et al., "Endothelial Injury in a Transforming Growth Factor β-Dependent Mouse Model of Scleroderma Induces Pulmonary Arterial Hypertension", Arthritis & Rheumatism 65(11):2928-2939 (2013).
Gong et al., "Hypoxia induces downregulation of PPAR-γ in isolated pulmonary arterial smooth muscle cells and in rat lung via transforming growth factor-β signaling", American Journal of Physiology-Lung Cellular and Molecular Physiology 301:L899-L907 (2011).
Graham et al., "Transforming Growth Factor-β Signaling Promotes Pulmonary Hypertension Caused by Schistosoma Mansoni", Circulation 128:1354-1364 (2013).

Harrison et al., "Transforming Growth Factor-β Receptor Mutations and Pulmonary Arterial Hypertension in Childhood", Circulation 111:435-441 (2005).
Jasinska-Stroschein et al., "The current approach into signaling pathways in pulmonary arterial hypertension and their implications in novel therapeutic strategies", Pharmacological Reports 1-13 (2014).
Long et al., "Altered Bone Morphogenetic Protein and Transforming Growth Factor-β Signaling in Rat Models of Pulmonary Hypertension: Potential for Activin Receptor-Like Kinase-5 Inhibition in Prevention and Progression of Disease", Circulation 119:566-576 (2009).
Montani et al., "Targeted therapies in pulmonary arterial hypertension", Pharmacology & Therapeutics 141:172-191 (2014).
Nasim et al., "BMPR-II deficiency elicits pro-proliferative and anti-apoptotic response through the activation of TGFβ-TAK1-MAPK pathways in PAH", Human Molecular Genetics 21(11):2548-2558 (2012).
Perkett et al., "Transforming Growth Factor-β Activity in Sheep Lung Lymph during the Development of Pulmonary Hypertension", Journal of Clinical Investigation 86:1459-1464 (1990).
Upton et al., "The transforming growth factor-β-bone morphogenetic protein type signaling pathway in pulmonary vascular homeostasis and disease", Experimental Physiology 98(8):1262-1266 (2013).
Upton et al., "Transforming Growth Factor-β1 Represses Bone Morphogenetic Protein-Mediated Smad Signaling in Pulmonary Artery Smooth Muscle Cells via Smad3", American Journal of Respiratory Cell and Molecular Biology 49 (6):1135-1145 (2013).
Zaiman et al., "Role of the TGF-β/ALK5 Signaling Pathway in Monocrotaline-induced Pulmonary Hypertension", American Journal of Respiratory and Critical Care Medicine 177:896-905 (2008).
Hatton et al., "Transforming growth factor signalling: a common pathway in pulmonary arterial hypertension and systemic sclerosis." International Journal of Clinical Practice 65:35-43 (2011).
Gordon et al., "Role of transforming growth factor-beta superfamily signaling pathways in human disease", Biochimica et Biophysica Acta, 1782(4): 197-228 (2008).
Ogo et al., "Inhibition of Overactive Transforming Growth Factor-β Signaling by Prostacyclin Analogs in Pulmonary Arterial Hypertension", Am J Respir Cell Mol Biol. 48(6):733-741 (2013).
Cao et al., "Changes of calponin and TGFbeta1 in pulmonary artery smooth muscle of pulmonary artery hypertension rats." Chinese Pharmacological Bulletin 23(2):277-278 (2007).
Anderton et al., "Induction of heart valve lesions by small-molecule ALK5 inhibitors." Toxicologic Pathology 39(6):916-924 (2011).
Grafe et al., "Excessive transforming growth factor-β signaling is a common mechanism in osteogenesis imperfecta." Nature Medicine 20(6):670-675 (2014).
Thomas et al., "Activin-like kinase 5 (ALK5) mediates abnormal proliferation of vascular smooth muscle cells from patients with familial pulmonary arterial hypertension and is involved in the progression of experimental pulmonary arterial hypertension induced by monocrotaline." The American Journal of Pathology 174(2):380-389 (2009).

* cited by examiner

Vehicle

TGFBRII-Fc

B

METHODS FOR TREATING PULMONARY HYPERTENSION WITH A TGF-BETA TYPE II RECEPTOR-FC FUSION PROTEIN

CROSS-REFERENCE TO RELATED APPLICATIONS

The instant application contains a Sequence Listing which has been submitted electronically in ASCII format and is hereby incorporated by reference in its entirety. Said ASCII copy, created on Jan. 9, 2015, is named 043214-079971-PCT_SL.txt and is 61,143 bytes in size.

SEQUENCE LISTING

This Application is a 35 U.S.C. § 371 National Phase Entry Application of International Application No. PCT/US14/66776 filed Nov. 21, 2014, which designates the U.S. and claims the benefit under 35 U.S.C. § 119(e) of U.S. Provisional Patent Application Ser. No. 61/907,260 filed Nov. 21, 2013, the contents of each of which are incorporated herein by reference in their entireties.

STATEMENT REGARDING FEDERALLY-SPONSORED RESEARCH

This invention was made with government support under 5R01AR057374 awarded by the NIH. The government has certain rights in the invention.

FIELD OF INVENTION

The present invention generally relates to the field of medicine and cardiovascular and pulmonary diseases.

BACKGROUND

All publications herein are incorporated by reference to the same extent as if each individual publication or patent application were specifically and individually indicated to be incorporated by reference. The following description includes information that may be useful in understanding the present invention. It is not an admission that any of the information provided herein is prior art or relevant to the presently claimed invention, or that any publication specifically or implicitly referenced is prior art.

Many pathological processes and undesirable biological processes occur via ligand binding to cell surface receptors and excessive/overactive signaling. Thus, compositions and methods aimed at reducing or otherwise favorably modulating such binding and signaling can be useful.

The TGF-β superfamily includes a number of ligands of biological significance. TGF-β and Activin play important pathogenic roles in many diseases, including the progression of cancer and uncontrolled fibrosis, such as kidney, lung and liver fibrotic diseases. Myostatin/GDF8 is another important ligand, which is related to Activin, and which shares binding to the same Type II receptor (ActivinRIIb). Myostatin is a powerful inhibitor of skeletal muscle growth and is a validated therapeutic target for muscle wasting diseases such as muscular dystrophy. Additional ligands in the TGF-β family include bone morphogenetic proteins (BMP), which have been implicated in cardiovascular diseases. For example, high levels of both BMP2 and BMP4 have been found in calcified atherosclerotic plaques and diseased aortic valves.

Methods have been developed to reduce ligand binding by trapping a ligand and preventing its interaction with cell surface receptors. Principal agents that target these ligands are ligand traps/antagonists that bind and sequester ligand. Two examples are: (1) anti-ligand antibodies and (2) soluble receptor ectodomains.

Inhibition of certain ligands has been reported using anti-ligand antibodies that trap and neutralize the ligand directly. Soluble versions of receptor ectodomains antagonize ligands directly by binding to them and preventing them from interacting with cell surface receptors. In the case of TGF-β, in animal models, expression of a TGF-β receptor type II (TβRII) ectodomain (ED) partially restored host immunity and promoted tumor clearance, indicating that receptor ectodomain-mediated neutralization of TGF-β inhibits tumor progression. Unfortunately, it has been demonstrated that monovalent TβRII-ED has less than optimal efficacy with respect to antagonizing TGF-β. Attempts to overcome this issue led to the production of bivalent artificially dimerized versions of TβRII-ED, which are dimerized via fusion to either coiled-coil domains or the Fc domain of IgG. This dimerization improved the antagonist effect. It has been demonstrated that non-covalent dimerization of TβRII-ED (for example, via fusion to heterodimerizing coil strands (coiled-coil TβRII-ED)), greatly enhances the antagonist potency of TβRII-ED (De Crescenzo et al., 2004, J. Biol, Chem. 279: 26013). A significant disadvantage of the coiled-coil fused dimer is that the non-covalent nature of the dimerization domain limits its potency, i.e. it dissociates at low concentrations such that a large portion of the coil-fused receptor ectodomain will be acting as a monomer rather than a dimer. Use of the Fc domain of IgG provides a covalent interaction, but at the cost of large size.

Importantly, among the obstacles to the clinical deployment of the TGFβRI inhibitors developed so far for treating PH has been toxicity, including hemorrhagic valve necrosis.

In view of the shortcomings of the therapeutic approaches attempted thus far, there is clearly a need in the art for receptor-based traps/neutralizers that can antagonize ligand activity and have the potential to act as therapeutic or diagnostic (imaging or non-imaging) agents for diseases/disorders caused by over-production/activity of the target ligands described herein.

SUMMARY OF THE INVENTION

The following embodiments and aspects thereof are described and illustrated in conjunction with systems, compositions and methods which are meant to be exemplary and illustrative, not limiting in scope.

Various embodiments of the present invention describe a pharmaceutical composition including a TGF-β ligand trap. In some embodiments, the TGF-β ligand trap is a soluble recombinant TGF-β type II receptor Fc-fusion protein (TGFBRII-Fc). In certain embodiments, the TGFBRII-Fc fusion protein comprises or consists of an amino acid sequence that is at least 80%, 85%, 90%, 95%, 96%, 97%, 98%, 99% or 100% identical to the amino acid sequence of SEQ ID NO:1.

Various embodiments of the present invention describe a method for treating, preventing, or reducing the progression rate of pulmonary hypertension (PH) in a subject. In some embodiments, the method includes administering a therapeutically effective amount of a TGF-β ligand trap to the subject, thereby treating, preventing, or reducing the progression rate of PH in the subject.

Various embodiments of the present invention describe a method of treating, preventing, or reducing the progression rate of pulmonary vascular remodeling in a subject. In some embodiments, the method includes administering a therapeutically effective amount of a TGF-β ligand trap to the subject, thereby treating, preventing, or reducing the progression rate of pulmonary vascular remodeling in the subject.

Various embodiments of the present invention describe a method of treating, preventing, or reducing the progression rate of pulmonary fibrosis in a subject. In some embodiments, the method includes administering a therapeutically effective amount of a TGF-β ligand trap to the subject, thereby treating, preventing, or reducing the progression rate of pulmonary fibrosis in the subject.

Various embodiments of the present invention describe a method of treating, preventing, or reducing the progression rate of right ventricular hypertrophy in a subject. In some embodiments, the method includes administering a therapeutically effective amount of a TGF-β ligand trap to the subject, thereby treating, preventing, or reducing the progression rate of right ventricular hypertrophy in the subject.

Various embodiments of the present invention describe a method of treating, preventing, or reducing the progression rate of a disease associated with excessive TGF-β signaling in a subject. In some embodiments, the method includes administering a therapeutically effective amount of a TGF-β ligand trap to the subject, thereby treating, preventing, or reducing the progression rate of the disease in the subject.

Various embodiments of the present invention describe a method of treating, preventing, or reducing the progression rate of a disease associated with excessive GDF15 signaling in a subject. In some embodiments, the method includes administering a therapeutically effective amount of a TGF-β ligand trap to the subject, thereby treating, preventing, or reducing the progression rate of the disease in the subject.

Various embodiments of the present invention describe a method of treating, preventing, or reducing the progression rate of a disease associated with excessive PAI-1 signaling in a subject. In some embodiments, the method includes administering a therapeutically effective amount of a TGF-β ligand trap to the subject, thereby treating, preventing, or reducing the progression rate of the disease in the subject.

Various embodiments of the present invention describe a method of reducing right ventricular systolic pressure in a subject. In some embodiments, the method includes administering a therapeutically effective amount of a TGF-β ligand trap to the subject, thereby reducing right ventricular systolic pressure in the subject.

Various embodiments of the present invention describe a method of imaging/detecting TGF-β ligand in a subject, including administering a quantity of a TGF-β ligand trap linked to an imaging molecule to the subject.

BRIEF DESCRIPTION OF THE DRAWINGS

Exemplary embodiments are illustrated in referenced figures. It is intended that the embodiments and figures disclosed herein are to be considered illustrative rather than restrictive.

FIG. 2A-2C demonstrate, in accordance with an embodiment of the invention, TGFBRII-Fc selectively inhibits the signaling of TGFβ1, TGFβ3, and GDF15 in human pulmonary artery smooth muscle cells (PASMC). Cultured PASMC were deprived of serum and incubated with BMP4, TGFβ1, TGFβ2, TGFβ3, and GDF15 ligands at various concentrations for 30 minutes. Western blot and qPCR were performed to assess the ability of TGFBRII-Fc to modulate signaling activity in vitro. FIG. 2D-2F demonstrate, in accordance with an embodiment of the invention, TGFBRII-Fc selectively inhibits TGFβ1 and GDF15 signaling in vascular smooth muscle cells. (FIG. 2D) Human aortic smooth muscle cells were deprived of serum overnight, and then incubated with BMP4, TGFβ1, TGFβ2, or GDF15 at indicated concentrations for 30 min, and analyzed by immunoblot for phosphorylation of Smads 1, 2, 3 and 5 as shown. TGFβ1, TGFβ2, and GDF15 elicited activation of Smad2 and Smad3 in a dose dependent fashion, and Smads 1 and 5 to a lesser extent, whereas BMP4 only activated Smads 1 and 5. (FIG. 2E-FIG. 2F) HASMCs were deprived of serum, pretreated with TGFBRII-Fc (2000 ng/ml) or vehicle followed by incubation with TGFβ1 (1 ng/ml), TGFβ2 (1 ng/ml), or GDF15 (30 ng/ml) for 2 hours. Analysis of gene expression by qRT-PCR revealed potent inhibition of GDF15 and TGFβ1-induced PAI-1 and Id1 mRNA expression, but not that of TGFβ2 (n=3-5 samples each, *p<0.05, **p<0.01 compared to vehicle).

FIGS. 8A and 8B show the amino acid sequences of human IgG1, IgG2, IgG3 and IgG4 hinge (FIG. 8A) and Fc (FIG. 8B) domains. (IgG1 hinge domain (SEQ ID NO:65); IgG2 hinge domain (SEQ ID NO:66); IgG3 hinge domain (SEQ ID NO: 67); IgG4 hinge domain (SEQ ID NO: 68); FIG. 8B is shown in same order as FIG. 8A: IgG1 Fc domain (SEQ ID NO:69), i.e. first line of aa's; IgG2 Fc domain (SEQ ID NO:70) i.e. second line of aa's; IgG3 Fc domain (SEQ ID NO: 71) i.e. third line of aa's; IgG4 Fc domain (SEQ ID NO: 72), i.e. fourth line of aa's. The amino acid residues shown in FIG. 8A and FIG. 8B are numbered according to the numbering system of Kabat EU. Isotype sequences are aligned with the IgG1 sequence by placing the first and last cysteine residues of the respective hinge regions, which form the inter-heavy chain S—S bonds, in the same positions. For FIG. 8B, residues in the CH2 domain are indicated by a plus sign (+), while residues in the CH3 domain are indicated by a squiggly line. Any Fc domain can be used in methods of the invention, all antibody sequences can be aligned as described in FIG. 8 providing guidance for the various FC domains.

FIG. 9A control. FIG. 9B TGFBRII-Fc-treated.

DETAILED DESCRIPTION OF THE INVENTION

Figures 1A, 1B:
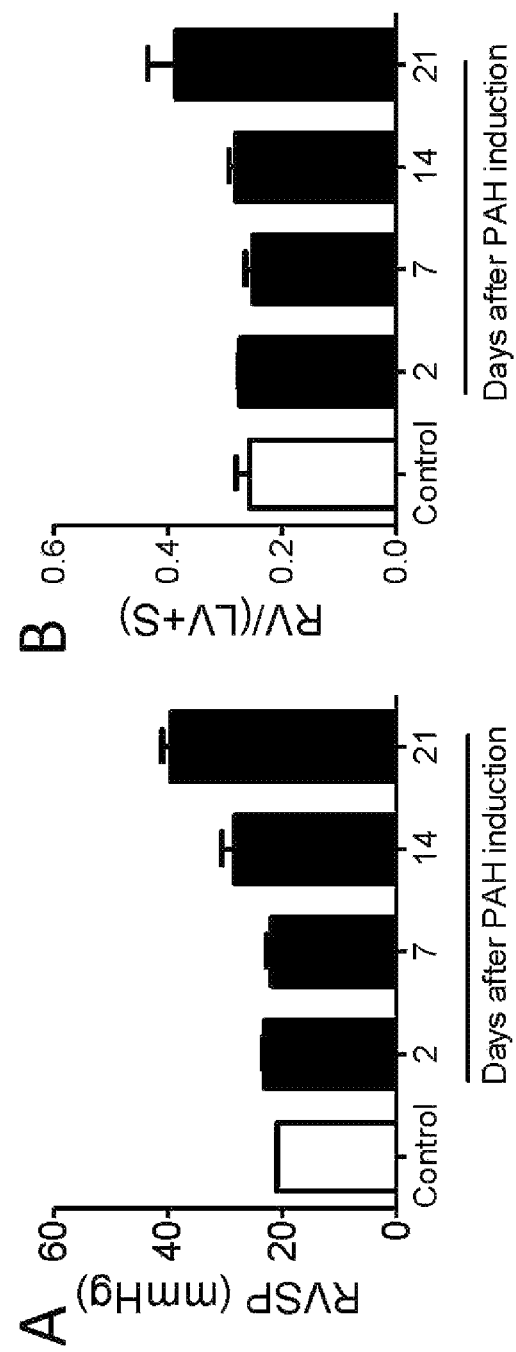
FIGS. 1A to 1E are graphs that demonstrate, in accordance with an embodiment of the invention, monocrotaline (MCT) induced pulmonary hypertension in rats is associated with increased PAI-1 and decreased Id1 transcriptional activity. Changes in right ventricular systolic pressure (RVSP, FIG. 1A) and right ventricular hypertrophy (RVH, FIG. 1B) were measured at various intervals after treatment of Sprague Dawley rats with MCT (40 mg/kg SC). RVSP was measured by right ventricular catheterization, and RVH was determined by the ratio of the weight of the right ventricular (RV) free wall to the sum of the left ventricular and septal (LV+S) walls (n=3 per time point). Quantitative RT-PCR of lungs of MCT-treated rats revealed elevated PAI-1 transcription reflecting increased TGF-β signaling (FIG. 1C), the levels of which correlated directly with the degree of PH based on RVSP (FIG. 1D & FIG. 1E). In contrast, decreased expression of Bmpr2 and its transcriptional target Id1 were observed, with levels which both correlated inversely with RVSP. (n=5-6, *p<0.05 and **p<0.01 compared to control rats).
Figures 1C, 1D, 1E:
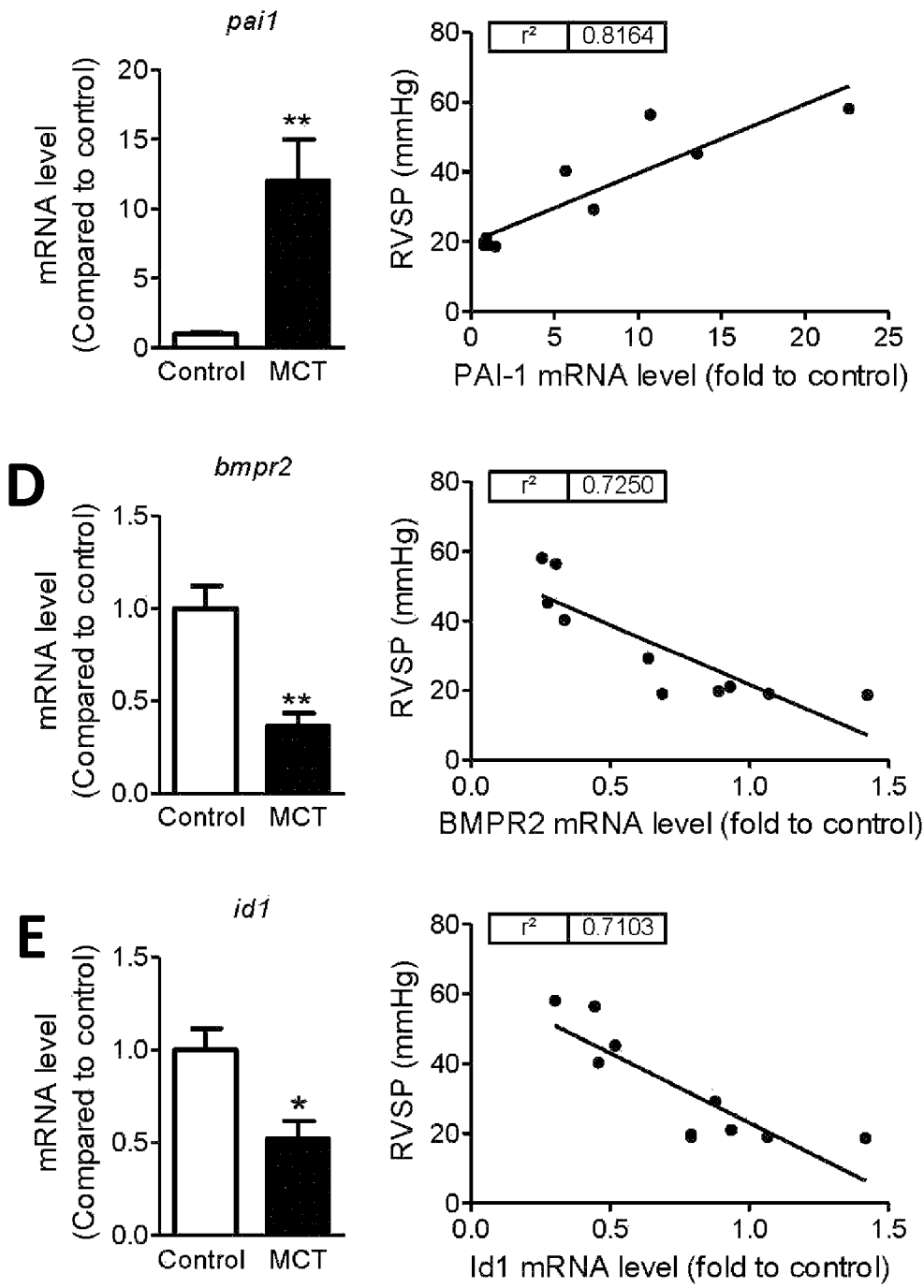
Figure 2:
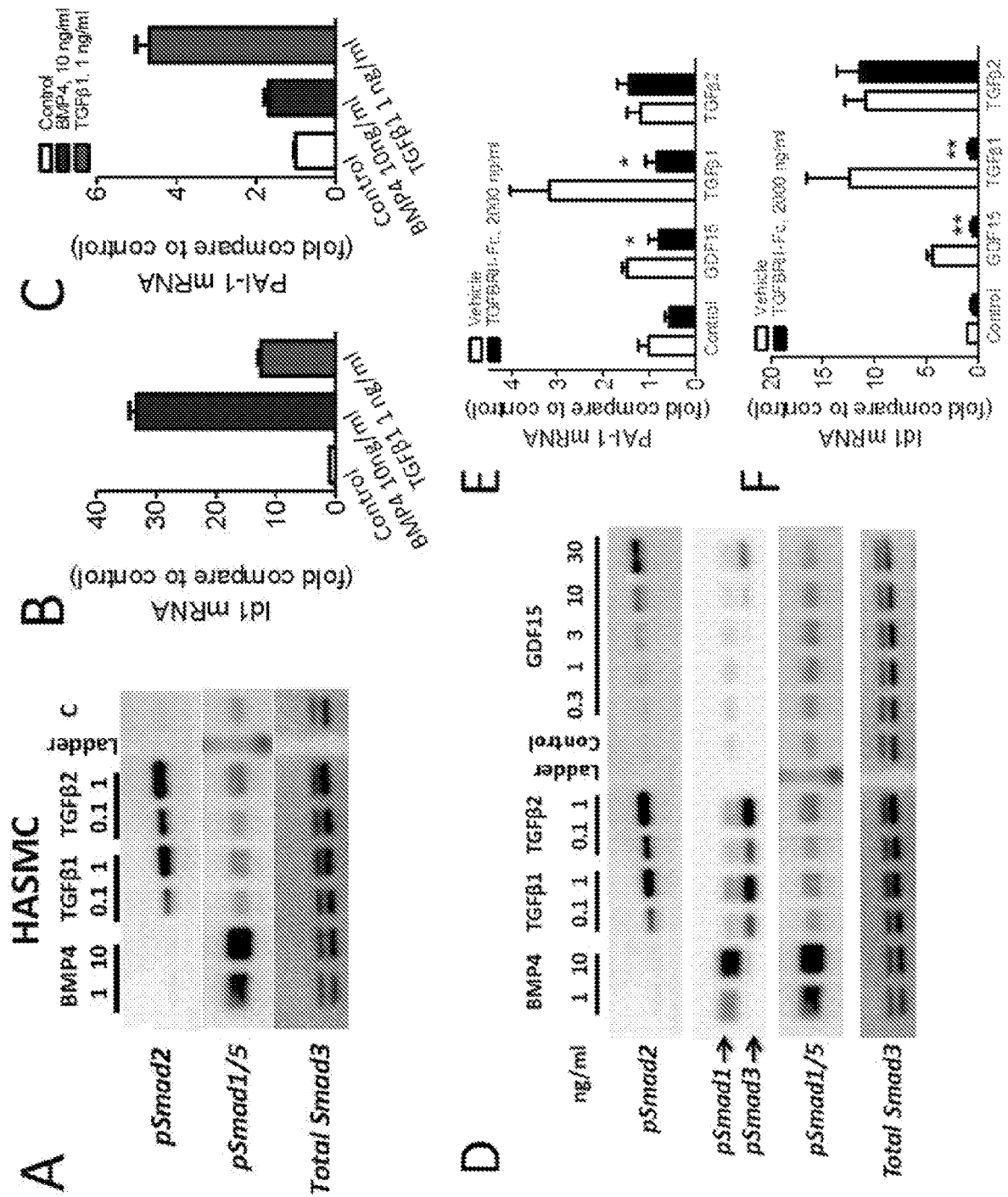
FIGS. 2A to 2F show immunoblots and graphs.

All references cited herein are incorporated by reference in their entirety as though fully set forth. Unless defined otherwise, technical and scientific terms used herein have the same meaning as commonly understood by one of ordinary skill in the art to which this invention belongs. Singleton et al., *Dictionary of Microbiology and Molecular Biology* 3$^{rd}$ ed., J. Wiley & Sons (New York, N.Y. 2001); March, *Advanced Organic Chemistry Reactions, Mechanisms and Structure* 5$^{th}$ ed., J. Wiley & Sons (New York, N.Y. 2001); and Sambrook and Russel, *Molecular Cloning: A Laboratory Manual* 3rd ed., Cold Spring Harbor Laboratory Press (Cold Spring Harbor, N.Y. 2001), provide one skilled in the art with a general guide to many of the terms used in the present application.

For references on how to prepare antibodies, see for example D. Lane, *Antibodies: A Laboratory Manual* (Cold Spring Harbor Press, Cold Spring Harbor N.Y., 1988); Kohler and Milstein, (1976) Eur. J. Immunol. 6: 511; Queen et al. U.S. Pat. No. 5,585,089; and Riechmann et al., Nature 332: 323 (1988). The practice of the present invention will employ, unless otherwise indicated, conventional techniques of molecular biology (including recombinant techniques), microbiology, cell biology, biochemistry, nucleic acid chemistry, and immunology, which are within the skill of the art. Such techniques are explained fully in the literature, such as, *Current Protocols in Immunology* (J. E. Coligan et al., eds., 1999, including supplements through 2011); *Current Protocols in Molecular Biology* (F. M. Ausubel et al., eds., 1987, including supplements through 2011); Short Protocols in Molecular Biology, F. M. Ausubel et al., eds., fifth edition 2002, including supplements through 2011; *Molecular Cloning: A Laboratory Manual*, third edition (Sambrook and Russel, 2001); *PCR: The Polymerase Chain Reaction*, (Mullis et al., eds., 1994); *The Immunoassay Handbook* (D. Wild, ed., Stockton Press NY, 1994); Bioconjugate Techniques (Greg T. Hermanson, ed., Academic Press, 1996); *Methods of Immunological Analysis* (R. Masseyeff, W. H. Albert, and N. A. Staines, eds., Weinheim: VCH Verlags gesellschaft mbH, 1993), Harlow and Lane *Using Antibodies: A Laboratory Manual* Cold Spring Harbor Laboratory Press, Cold Spring Harbor, N.Y., 1999; and Beaucage et al. eds., Current Protocols in Nucleic Acid Chemistry John Wiley & Sons, Inc., New York, 2000).

One skilled in the art will recognize many methods and materials similar or equivalent to those described herein, which could be used in the practice of the present invention. Other features and advantages of the invention will become apparent from the following detailed description, taken in conjunction with the accompanying drawings, which illustrate, by way of example, various features of embodiments of the invention. Indeed, the present invention is in no way limited to the methods and materials described. For purposes of the present invention, certain terms are defined below.

"Beneficial results" may include, but are in no way limited to, lessening or alleviating the severity of the disease condition, preventing the disease condition from worsening, curing the disease condition, preventing the disease condition from developing, lowering the chances of a patient developing the disease condition and prolonging a patient's life or life expectancy. In various embodiments, the disease condition is pulmonary hypertension, pulmonary vascular remodeling, pulmonary fibrosis, right ventricular hypertrophy, diseases associated with excessive TGF-β signaling, diseases associated with excessive GDF15 signaling, and diseases associated with excessive PAI-1 signaling.

"Treatment" and "treating", as used herein refer to both therapeutic treatment and prophylactic or preventative measures, wherein the object is to slow down (lessen) the targeted pathologic condition, prevent the pathologic condition, pursue or obtain beneficial results, or lower the chances of the individual developing the condition even if the treatment is ultimately unsuccessful. Those in need of treatment include those already with the condition as well as those prone to have the condition or those in whom the condition is to be prevented.

"Pulmonary hypertension" (PH) as used herein can include an increase of blood pressure in the pulmonary artery (pulmonary arterial hypertension), pulmonary vein, or pulmonary capillaries, together known as the lung vasculature, leading to shortness of breath, dizziness, fainting, leg swelling and other symptoms. PH can be a severe disease with a markedly decreased exercise tolerance and heart failure. PH can be one of at least five different possible types, including: arterial, venous, hypoxic, thromboembolic or miscellaneous.

A "TGF-β ligand trap" as used herein refers to a protein that is capable of trapping a TGF-β ligand, even if only transiently, thereby modulating the ligand's ability to interact with one or more additional molecules.

In some embodiments, the TGF-β ligand can mean a ligand selected from among TGF-β1, TGF-β2, TGF-β3, and GDF 15.

An example of a TGF-β ligand trap includes, but is in no way limited to, a soluble recombinant TGF-β receptor Fc-fusion protein, which includes the TGF-β ligand binding domain of a TGF-β receptor and the Fc domain of an immunoglobin.

Accordingly, in one embodiment a method of treating, preventing, or reducing the progression rate of a pulmonary hypertension (PH) in a subject is provided. The method comprises administering a therapeutically effective amount of a TGF-β ligand trap to the subject, thereby treating, preventing, or reducing the progression rate of a PH in the subject, wherein the TGF-β ligand trap comprises 1) a TGF-β ligand binding domain of a TGF β receptor and 2) a Fc domain of an immunoglobulin, and 3) optionally a linker (an immunoglobulin linker or other linker) between the ligand binding domain and the Fc domain.

In one embodiment, the TGF-β ligand binding domain of a TGF β receptor comprises SEQ ID NO: 63, or portion thereof, or variant thereof:

```
                                          (SEQ ID NO: 63)
TIPPHVQKSV NNDMIVTDNN GAVKFPQLCK FCDVRFSTCD

NQKSCMSNCS ITSICEKPQE VCVAVWRKND ENITLETVCH

DPKLPYHDFI LEDAASPKCI MKEKKKPGET FFMCSCSSDE

CNDNIIFSEE YNTSNPD.
```

In one embodiment, the TGF-β ligand binding domain of a TGF β receptor comprises SEQ ID NO: 3, or SEQ ID NO; 4, or SEQ ID NO: 5, or portion thereof, or variant thereof:

In one embodiment, the Fc domain comprises SEQ ID NO: 64, or fragment/portion of SEQ ID NO: 64, or variant thereof

```
SEQ ID NO: 64:
                                          (SEQ ID NO: 64)
ECPPCPAP PVAGPSVFLF PPKPKDTLMI SRTPEVTCVV

VDVSHEDPEV QFNWYVDGVE VHNAKTKPRE EQFNSTFRVV

SVLTVVHQDW LNGKEYKCKV SNKGLPAPIE KTISKTKGQP

REPQVYTLPP SREEMTKNQV SLTCLVKGFY PSDIAVEWES

NGQPENNYKT TPPMLDSDGS FFLYSKLTVD KSRWQQGNVF

SCSVMHEALH NHYTQKSLSL SPGK
```

Further, exemplary Fc domains are described in FIG. 1B, e.g. SEQ ID NO:'s 69, 70, 71 and 72. In certain embodiments the Fc domain comprises SEQ ID NO: 69, SEQ ID NO: 70, SEQ ID NO: 71, or SEQ ID NO: 72, or comprise a fragment of SEQ ID NO: 69, SEQ ID NO: 70, SEQ ID NO: 71, or SEQ ID NO: 72, or a variant of SEQ ID NO: 69, SEQ ID NO: 70, SEQ ID NO: 71, or SEQ ID NO: 72.

It is within the capacity of one of ordinary skill in the art to select suitable binding domains in light of the disclosure herein. In some instances, the binding domains may be selected from the ectodomains of the TGF-β type II and TGF-β type I receptors. One non-limiting example is a soluble recombinant TGF-β type II receptor Fc-fusion protein (TGFBRII-Fc).

In a further example, the natural receptors from which the polypeptide binding domain is designed may be TβR-I-ED or TβR-II-ED.

In one embodiment the TGF-β ligand binding domain of a TGF β receptor comprises a sequence of the TGF-β type I receptor ectodomain, or portion of ectodomain, for example SEQ ID NO: 73, or portion thereof 1 GVQVETISPG DGRTFPKRGQ TCVVHYTGML EDGK-KFDSSR DRNKPFKFML GKQEVIRGWE EGVAQMS-VGQ RAKLTISPDY AYGATGHPGI IPPHATLVFD VELLKLE (SEQ ID NO: 73), or e.g. SEQ ID NO: 74, or fragment/portion thereof, EDPSLDRPFI SEGTTLKDLI YDMTTSGSGS GLPLLVQRTI ARTIVLQESI GKGRF-GEVWR GKWRGEEVAV KIFSSREERS WFREAEIYQT VMLRHENILG FIAADNKDNG TWTQLWLVSD YHE-HGSLFDY LNRYTVTVEG MIKLALSTAS GLAHLH-MEIV GTQGKPAIAH RDLKSKNILV KKNGTCCIAD LGLAVRHDSA TDTIDIAPNH RVGTKRYMAP EVLDDSINMK HFESFKRADI YAMGLVFWEI ARRC-SIGGIH EDYQLPYYDL VPSDPSVEEM RKVVCEQKLR PNIPNRWQSC EALRVMAKIM RECWYANGAA RLTALRIKKT LSQLSQQEGI KM (SEQ ID NO: 74) (Chain A, Cytoplasmic Domain Of Unphosphorylated Type I Tgf-Beta Receptor Crystallized Without Fkbp12 GeneBankACCESSION 1IAS_A GI:15988007.

In one embodiment the TGF-β ligand binding domain of a TGF β receptor comprises a sequence of the TβR-III-ED, or portion of SEQ ID NO: 75; 1 MTSHYVIAIF ALMSSCLATA GPEPGALCEL SPVSASHPVQ ALMESFTVLS GCASRGTTGL PQEVHVLNLR TAGQGPGQLQ REVTLHLNPI SSVHIHHKSV VFLLNSPHPL VWHLKTERLA TGVSRLFLVS EGSVVQFSSA NFSLTAETEE RNFPHGNEHL LNWARKEYGA VTSFTELKIA RNIYIKVGED QVFPPKCNIG KNFLSLNYLA EYLQPKAAEG CVMSSQPQNE EVHIIELITP NSNPYSAFQV DITIDIRPSQ EDLEVVKNLI LILKCKKSVN WVIKSFDVKG SLKIIAPNSI GFGKESERSM TMTKSIRDDI PSTQGNLVKW ALDNGYSPIT SYTMAPVANR FHLRLENNEE MGDEEVHTIP PELRILLDPG ALPALQNPPI RGGEGQNGGL PFPFPDISRR VWNEEGEDGL PRPKDPVIPS IQLFPGLREP EEVQGSVDIA LSVKCDNEKM IVAVEKDSFQ ASGYSGMDVT LLDPTCKAKM NGTHFVLESP LNGCGTRPRW SALDGVVYYN SIVIQVPALG DSSGWPDGYE DLESGDNGFP GDMDEGDASL FTRPEIVVFN CSLQQVRNPS SFQEQPHGNI TFNMELYNTD LFLVPSQGVF SVPENGHVYV EVSVTKAEQE LGFAIQTCFI SPYSNPDRMS HYTIIENICP KDESVKFYSP KRVHFPIPQA DMDKKRFSFV FKPVFNTSLL FLQCELTLCT KMEKHPQKLP KCVPPDEACT SLDASIIWAM MQNKKTFTKP LAVIHHEAES KEKGPSMKEP NPISPPIFHG LDTLT (SEQ ID NO: 75), (also known as soluble TGF-β receptor III, for example human recombinant soluble TGF-βsRIII is described in Moren A, et al. Molecular cloning and characterization of the human and porcine transforming growth factor-beta type III receptors, 1992, J. Biochem. Biophys. Res. Commun. 189 (1), 356-362).

Recombinant soluble TGF-βR type II cDNA is described in Melissa A. Rowland-Goldsmith et al. Soluble Type II Transforming Growth Factor-β (TGF-β) Receptor Inhibits TGF-β Signaling in COLO-357 Pancreatic Cancer Cells in Vitro and Attenuates Tumor Formation 1, 2001, Clin Cancer Res, 7: 2931. The complete cDNA of human TβRII was used as the template for PCR amplification of the coding sequence of the extracellular domain of TβRII (nucleotides 1-477 including the signal sequence). PCR was performed using the sense primer, 5'-AAGCTTGCCGCCGCCATGGGTCG (SEQ ID NO: 76), and antisense primer, 5'-CTGGAATTCGTCAGGATTGCTGG (SEQ ID NO: 77). SEQ ID NO: 78 is an example of Type II Transforming Growth Factor-β (TGF-β) Receptor extracellular domain:

```
                                        (SEQ ID NO 78)
MGRGLLRGLW PLHIVLWTRI ASTIPPHVQK SVNNDMIVTD

NNGAVKFPQL CKFCDVRFST CDNQKSCMSN CSITSICEKP

QEVCVAVWRK NDENITLETV CHDPKLPYHD FILEDAASPK

CIMKEKKKPG ETFFMCSCSS DECNDNIIFS EEYNTSNPDL

LLVIFQVTGI SLLPPLGVAI SVIIIFYCYR VNRQQKLSST

WETGKTRKLM EFSEHCAIIL EDDRSDISST CANNINHNTE

LLPIELDTLV GKGRFAEVYK AKLKQNTSEQ FETVAVKIFP

YEEYASWKTE KDIFSDINLK HENILQFLTA EERKTELGKQ

YWLITAFHAK GNLQEYLTRH VISWEDLRKL GSSLARGIAH

LHSDHTPCGR PKMPIVHRDL KSSNILVKND LTCCLCDFGL

SLRLDPTLSV DDLANSGQVG TARYMAPEVL ESRMNLENVE

SFKQTDVYSM ALVLWEMTSR CNAVGEVKDY EPPFGSK.
```

The complete extracellular portion of the TGF beta receptors typically includes unstructured segments flanking their folded ligand-binding domain. These unstructured extracellular portions are apparent from the experimentally determined 3D structures available from the PDB database (Berman et al., 2000, Nucl. Acid Res. 28: 235), e.g., crystal structures for type II TGF-β receptor ectodomain (Hart et al., 2002 Nat. Struct. Biol. 9: 203; Boesen et al., 2002, Structure 10: 913; Groppe et al., 2008, Mol. Cell 29: 157), type I TGF-β receptor ectodomain (Groppe et al., 2008, Mol. Cell 29:157), or the NMR structure of the type II TGF-β receptor ectodomain (Deep et al., 2003, Biochemistry 42: 10126. One of skill in the art is well versed in identifying ligand binding domains of the TGF beta receptors. For the TGF beta traps, the binding of ligand can be confirmed using standard ligand binding assays, well known to those of skill in the art, e.g. radio ligand binding assays (See e.g. Sittampalam, G. S.; Kahl, S. D.; Janzen, W. P. High-throughput screening: Advances in assay technologies, 1997, Current Opinion in Chemical Biology 1 (3): 384-391; and De Jong, L. A. A.; et al. Receptor-ligand binding assays: Technologies and Applications, 2005, Journal of Chromatography B 829 (1-2): 1-25).

"TGFBRII-Fc" as used herein refers to a fusion protein including the TGF-β ligand binding domain of a TGF-β type II receptor or a variant or biologically active portion thereof and the Fc domain of an immunoglobin. In various embodiments, between the TGF-β ligand binding domain and the Fc domain, a linker can be included. Also in accordance with the present invention, a fusion protein can include the entire extracellular portion of a TGF-β type II receptor or a variant thereof and the Fc domain of an immunoglobin. In some embodiments, a fusion protein can include part of the extracellular portion of a TGF-β type II receptor or a variant thereof and the Fc domain of an immunoglobin. Examples of variants can include, but are not limited to, those that include conservative amino acid mutations, SNP variants, and splicing variants. One non-limiting example is the IIb splicing variant of the TGF-β type II receptor. In various embodiments, the TGF-β ligand binding domain and/or the Fc domain may be modified, for example, to facilitate purification, so long as such modifications do not reduce the functions of these domains to unacceptable level.

The basic technology of Fc-fusions has been generally described in the art, for example, in Czajkowsky et al. Fc-fusion proteins: new developments and future perspectives, EMBO Mol Med. 2012 October; 4(10):1015-28, which is incorporated in its entirety by reference herein. The TGF-β type II receptor can be from a mammal. In some examples the receptor is from a human, monkey, ape, dog, cat, cow, horse, goat, sheep, pig, rabbit, mouse, or rat. The immunoglobin can be from a mammal. Merely by way of example, it can be from a human, monkey, ape, dog, cat, cow, horse, goat, sheep, pig, rabbit, mouse, or rat.

When referring to the antibody domains, the assignment of amino acids to each domain is in accordance with the definitions of Kabat (See, "*Sequences of Proteins of Immunological Interest*" by Elvin A. Kabat, Tai Te Wu, Kay S.

Gottesman, Carl Foeller 5th edition, Publication no. 91 3242. *National Institutes of Health*, Bethesda, Md., 1991, and earlier editions). Amino acids from the variable regions of the mature heavy and light chains of immunoglobulins are designated by the position of an amino acid in the chain. Kabat described numerous amino acid sequences for antibodies, identified an amino acid consensus sequence for each subgroup, and assigned a residue number to each amino acid. Kabat's numbering scheme is extendible to antibodies not included in his compendium by aligning the antibody in question with one of the consensus sequences in Kabat by reference to conserved amino acids. This method for assigning residue numbers has become standard in the field and readily identifies amino acids at equivalent positions in different antibodies, including chimeric or humanized variants. For example, an amino acid at position 50 of a human antibody light chain occupies the equivalent position to an amino acid at position 50 of a mouse antibody light chain.

As used herein, the term "Fc region," "Fc domain" or analogous terms are used to define CH2/CH3 C-terminal region of an IgG heavy chain. An example of the amino acid sequence containing the human IgG1 is shown in FIG. 8B. Although boundaries may vary slightly, as numbered according to the Kabat system, the Fc domain extends from amino acid 231 to amino acid 447 (amino acid residues in FIG. 8B are numbered according to the Kabat system: See Kabat et al., "Sequences of Proteins of Immunological Interest", 5th Ed. Public Health Service, NIH, MD (1991), which is herein incorporated by reference in its entirety.). FIG. 8B also provides examples of the amino acid sequences of the Fc regions of IgG isotypes IgG1, IgG2, IgG3, and IgG4.

The Fc region of an IgG comprises two constant domains, CH2 and CH3. The CH2 domain of a human IgG Fc region usually extends from amino acids 231 to amino acid 341 according to the numbering system of Kabat (FIG. 8B). The CH3 domain of a human IgG Fc region usually extends from amino acids 342 to 447 according to the numbering system of Kabat (FIG. 8B). The CH2 domain of a human IgG Fc region (also referred to as "Cγ2" domain) is unique in that it is not closely paired with another domain. Rather, two N-linked branched carbohydrate chains are interposed between the two CH2 domains of an intact native IgG.

Examples of TGFBRII-Fc include, but are not limited to, a protein having the sequence set forth in SEQ ID NO:1 or a variant thereof. In one embodiment, a variant of SEQ ID NO:1 includes a sequence with at least 80%, 85%, 90%, 95%, 98%, or 99% sequence identity to SEQ ID NO:1.

```
                                               (SEQ ID NO: 1)
TIPPHVQKSV NNDMIVTDNN GAVKFPQLCK FCDVRFSTCD

NQKSCMSNCS ITSICEKPQE VCVAVWRKND ENITLETVCH

DPKLPYHDFI LEDAASPKCI MKEKKKPGET FFMCSCSSDE

CNDNIIFSEE YNTSNPDTGG GVECPPCPAP PVAGPSVFLF

PPKPKDTLMI SRTPEVTCVV VDVSHEDPEV QFNWYVDGVE

VHNAKTKPRE EQFNSTFRVV SVLTVVHQDW LNGKEYKCKV

SNKGLPAPIE KTISKTKGQP REPQVYTLPP SREEMTKNQV

SLTCLVKGFY PSDIAVEWES NGQPENNYKT TPPMLDSDGS

FFLYSKLTVD KSRWQQGNVF SCSVMHEALH NHYTQKSLSL

SPGK.
```

In SEQ ID NO:1, amino acids 1-137 are a TGF-β ligand binding domain, amino acids 138-141 are a linker and amino acids 142-364 are an Fc domain. This exemplar TGFBRII-Fc can be expressed by a nucleic acid that includes a nucleotide sequence set forth in SEQ ID NO:2, or a degenerate variant thereof. A "degenerate variant" as used herein refers to a variant that has a mutated nucleotide sequence, but still encodes the same polypeptide due to the redundancy of the genetic code.

```
                                               (SEQ ID NO: 2)
  1 ATGGATGCAA TGAAGAGAGG GCTCTGCTGT GTGCTGCTGC TGTGTGGAGC

51 AGTCTTCGTT TCGCCCGGCG CCACGATCCC ACCGCACGTT CAGAAGTCGG

101 TTAATAACGA CATGATAGTC ACTGACAACA ACGGTGCAGT CAAGTTTCCA

151 CAACTGTGTA AATTTTGTGA TGTGAGATTT TCCACCTGTG ACAACCAGAA

201 ATCCTGCATG AGCAACTGCA GCATCACCTC CATCTGTGAG AAGCCACAGG

251 AAGTCTGTGT GGCTGTATGG AGAAAGAATG ACGAGAACAT AACACTAGAG

301 ACAGTTTGCC ATGACCCCAA GCTCCCCTAC CATGACTTTA TTCTGGAAGA

351 TGCTGCTTCT CCAAAGTGCA TTATGAAGGA AAAAAAAAG CCTGGTGAGA

401 CTTTCTTCAT GTGTTCCTGT AGCTCTGATG AGTGCAATGA CAACATCATC

451 TTCTCAGAAG AATATAACAC CAGCAATCCT GACACCGGTG GTGGAGTCGA

501 GTGCCCACCG TGCCCAGCAC CACCTGTGGC AGGACCGTCA GTCTTCCTCT

551 TCCCCCCAAA ACCCAAGGAC ACCCTCATGA TCTCCCGGAC CCCTGAGGTC

601 ACGTGCGTGG TGGTGGACGT GAGCCACGAA GACCCCGAGG TCCAGTTCAA

651 CTGGTACGTG GACGGCGTGG AGGTGCATAA TGCCAAGACA AAGCCACGGG

701 AGGAGCAGTT CAACAGCACG TTCCGTGTGG TCAGCGTCCT CACCGTCGTG

751 CACCAGGACT GGCTGAACGG CAAGGAGTAC AAGTGCAAGG TCTCCAACAA
```

```
 801 AGGCCTCCCA GCCCCCATCG AGAAAACCAT CTCCAAAACC AAAGGGCAGC

851 CCCGAGAACC ACAGGTGTAC ACCCTGCCCC CATCCCGGGA GGAGATGACC

901 AAGAACCAGG TCAGCCTGAC CTGCCTGGTC AAAGGCTTCT ACCCCAGCGA

951 CATCGCCGTG GAGTGGGAGA GCAATGGGCA GCCGGAGAAC AACTACAAGA

1001 CCACACCTCC CATGCTGGAC TCCGACGGCT CCTTCTTCCT CTACAGCAAG

1051 CTCACCGTGG ACAAGAGCAG GTGGCAGCAG GGGAACGTCT TCTCATGCTC

1101 CGTGATGCAT GAGGCTCTGC ACAACCACTA CACGCAGAAG AGCCTCTCCC

1151 TGTCTCCGGG TAAA
```

Figure 8A:
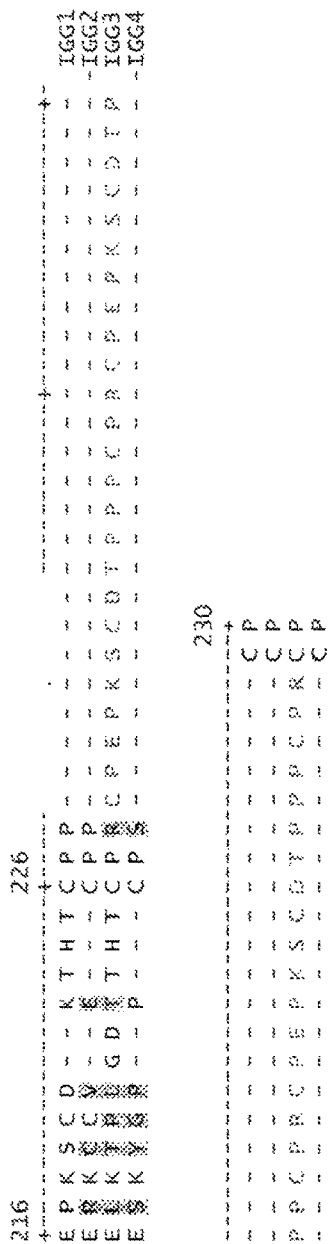

The "hinge region" or "hinge domain" of a heavy chain IgG is generally defined as stretching from Glu216 to Pro230 of human IgG1 using Kabat numbering. An example of the amino acid sequence of the human IgG1 hinge region is shown in FIG. 8A (amino acid residues in FIG. 8A are numbered according to the Kabat system). Hinge regions of other IgG isotypes may be aligned with the IgG1 sequence by placing the first and last cysteine residues forming inter-heavy chain S—S binds in the same positions as shown in FIG. 8A. In certain embodiments, the linker between the ligand binding domain and the Fc domain comprises a hinge region, e.g. any of SEQ ID NO: 65-68 (See FIG. 8A). In one embodiment, the linker comprises TGG G (SEQ ID NO: 79). In certain embodiments the linker comprises any of SEQ ID NO's: 6-48 (See Example 3).

One of skill in the art would readily appreciate that substantially identical peptides to those specifically described herein are contemplated and may include one or more conservative amino acid mutations. It is known in the art that one or more conservative amino acid mutations to a reference peptide may yield a mutant peptide with no substantial change in physiological, chemical, or functional properties, compared to the reference peptide; and in such a case, the reference and mutant peptides would be considered "substantially identical" polypeptides.

A conservative amino acid mutation may include the addition, deletion, or substitution of an amino acid. A conservative amino acid substitution is defined herein as the substitution of an amino acid residue for another amino acid residue with similar chemical properties (e.g. size, charge, or polarity). In a non-limiting example, a conservative mutation may be an amino acid substitution. Such a conservative amino acid substitution may substitute a basic, neutral, hydrophobic, or acidic amino acid for another of the same group.

As used herein, "basic amino acid" includes hydrophilic amino acids having a side chain pKa value of greater than 7, which are typically positively charged at physiological pH. Basic amino acids include histidine (His or H), arginine (Arg or R), and lysine (Lys or K). As used herein, "neutral amino acid" (also "polar amino acid") means hydrophilic amino acids having a side chain that is uncharged at physiological pH, but in which at least one bond in which the pair of electrons shared in common by two atoms is held more closely by one of the atoms. Polar amino acids include serine (Ser or S), threonine (Thr or T), cysteine (Cys or C), tyrosine (Tyr or Y), asparagine (Asn or N), and glutamine (Gln or Q). The term "hydrophobic amino acid" (also "non-polar amino acid") is meant to include amino acids exhibiting a hydrophobicity of greater than zero according to the normalized consensus hydrophobicity scale of Eisenberg (1984). Hydrophobic amino acids include proline (Pro or P), isoleucine (Ile or I), phenylalanine (Phe or F), valine (Val or V), leucine (Leu or L), tryptophan (Trp or W), methionine (Met or M), alanine (Ala or A), and glycine (Gly or G). "Acidic amino acid" refers to hydrophilic amino acids having a side chain pKa value of less than 7, which are typically negatively charged at physiological pH. Acidic amino acids include glutamate (Glu or E), and aspartate (Asp or D).

Sequence identity is used to evaluate the similarity of two sequences; it is determined by calculating the percent of residues that are the same when the two sequences are aligned for maximum correspondence between residue positions. Any known method may be used to calculate sequence identity; for example, computer software is available to calculate sequence identity. By way of non-limiting example, sequence identity can be calculated by software such as BLAST-P, Blast-N, or FASTA-N, or any other appropriate software that is known in the art. The substantially identical sequences of the present invention may be at least 80% identical. In other examples, the substantially identical sequences may be at least 80%, 85%, 90%, 95%, or 100% identical at the amino acid level to sequences described herein.

As indicated above, in various embodiments, between the TGF-β ligand binding domain and the Fc domain, there may be a linker. Provided herein are sequences of such linkers. In one embodiment, the linker is an unstructured and flexible polypeptide sequence. The linker region provides a segment that is distinct from the structured ligand binding and Fc domains and thus can be used for conjugation to accessory molecules (for example, molecules useful in increasing stability such as PEGylation moieties) or cargo molecules such as contrast agents for imaging and toxins without having to chemically modify the ligand binding and Fc domains. Conjugation methodologies are somewhat diverse, but typically can be performed using commercial kits that enable conjugation via common reactive groups such as primary amines, succinimidyl (NHS) esters and sulfhydral-reactive groups. Some non-limiting examples are: Alexa Fluor 488 protein labeling kit (Molecular Probes, Invitrogen detection technologies) and PEGylation kits (Pierce Biotechnology Inc.).

The linker may include an unstructured amino acid sequence that may be either the same as or derived from conservative modifications to the sequence of a natural unstructured region in the extracellular portion of the receptor for the ligand of interest or another receptor in the TGF-β superfamily. In other instances, such linkers may be entirely artificial in composition and origin but will contain amino acids selected to provide an unstructured flexible linker with a low likelihood of encountering electrostatic or steric hindrance complications when brought into close proximity to the ligand of interest.

The length of the linker is considered to be the number of amino acids between: (a) the C-terminal main chain carbon atom of the binding domain located at the linker's N-terminal end; and (b) the N-terminal main-chain nitrogen atom of binding domain located at the linker's C-terminal end. Linker length will be considered acceptable when it permits binding domains to bind their natural binding sites on their natural ligand. Examples of natural and artificial linker sequences of varying length are given in Table 2. For example, and without wishing to be limiting in any manner, the linker length may be between about 18-80 amino acids, 25-60 amino acids, 35-45 amino acids, or any other suitable length.

In some instances, it may be desirable to subject the polypeptide-based linking design of the ligand binding agents disclosed herein to optimization of characteristics desired for a particular application. For example, the linker may be modified in length and composition based on atomic-level simulations and knowledge-based design in order to improve binding affinity, specificity, immunogenicity and stability. This is applicable to a wide range of molecular systems exhibiting homomeric, heteromeric, dimeric and multimeric ligand-receptor structural characteristics. Additional different binding domains can be incorporated to generate multivalent traps with even higher binding potency.

Linkers may be designed to facilitate purification of the linker and/or ligand binding trap. The exact purification scheme chosen will determine what modifications are needed, for example and without wishing to be limiting, additions of purification "tags" such as His tags is contemplated; in other examples, the linker may include regions to facilitate the addition of cargo or accessory molecules. When such additions affect the unstructured nature of the linker or introduce potential electrostatic or steric concerns, appropriate increases to the linker length will be made to ensure that the binding domains are able to bind their sites on the ligand. In light of the methods and teachings herein, such determinations could be made routinely by one skilled in the art.

In an embodiment of the invention in which the ligand-binding domains and the linker contain primarily natural sequences they would not ordinarily be expected to be severely immunogenic or toxic in a typical patient.

Polypeptides of the invention can be useful as therapeutic agents that neutralize the action of disease-associated covalently-stabilized dimeric ligands such as growth factors. They may also have commercial potential for use as diagnostic agents to detect the presence of disease-associated covalently-stabilized dimeric ligands such as growth factors in imaging and non-imaging diagnostic applications.

The present invention also encompasses nucleotide sequences encoding polypeptides of the invention. These nucleotide sequences can be cloned and inserted into any suitable vector (including expression vector) and therefore are very amenable to production of polypeptides of the invention.

The term "vector," as used herein, refers to a carrier nucleic acid molecule into which a nucleic acid sequence can be inserted for introduction into a cell where it can be replicated. A nucleic acid sequence can be "exogenous," which means that it is foreign to the cell into which the vector is being introduced or that the sequence is homologous to a sequence in the cell but in a position within the host cell nucleic acid in which the sequence is ordinarily not found. Vectors include plasmids, cosmids, viruses (bacteriophage, animal viruses, and plant viruses), and artificial chromosomes (e.g., YACs). One of skill in the art would be well equipped to construct a vector through standard recombinant techniques (see, for example, Maniatis et al., 1988 and Ausubel et al., 1994, both of which are incorporated herein by reference). Additionally, the techniques described herein and demonstrated in the referenced figures are also instructive with regard to effective vector construction.

The term "expression vector" refers to any type of genetic construct comprising a nucleic acid coding for a RNA capable of being transcribed. In some cases, RNA molecules are then translated into a protein, polypeptide, or peptide. In other cases, these sequences are not translated, for example, in the production of antisense molecules or ribozymes. Expression vectors can contain a variety of "control sequences," which refer to nucleic acid sequences necessary for the transcription and possibly translation of an operably linked coding sequence in a particular host cell. In addition to control sequences that govern transcription and translation, vectors and expression vectors may contain nucleic acid sequences that serve other functions as well and are described infra.

The term "polypeptide" or "protein," as used herein, means a polymer of amino acids joined in a specific sequence by peptide bonds. As used herein, the term "amino acid" refers to either the D or L stereoisomer form of the amino acid, unless otherwise specifically designated.

A "biologically active" portion of a molecule, as used herein, refers to a portion of a larger molecule that can perform a similar function as the larger molecule. Merely by way of a non-limiting example, a biologically active portion of a protein is any portion of a protein which retains the ability to perform one or more biological functions of the full-length protein (e.g. binding with another molecule, phosphorylation, etc.), even if only slightly. As a non-limiting example, the ligand binding domain is a biological portion of a TGFβ receptor.

As used herein, the term "therapeutically effective amount" means the amount of a TGF-β ligand trap that attenuates or inhibits excessive TGF-β signaling and hence results in treating, preventing or slowing the progression rate of a disease condition described herein. An effective amount will vary, depending upon the pathology or condition to be treated, by the patient and his or her status, and other factors well known to those of skill in the art. Effective amounts are easily determined by those of skill in the art. In some embodiments a therapeutic dose is administered at an interval from every day to every month via the subcutaneous, intrathecal, convection-enhanced, intravenous or intra-arterial route at a dose ranging from 0.05 mg to 50 mg/kg of body weight, and optionally 1.0 mg to 10 mg/kg of body weight or 0.3 mg to 3.0 mg/kg of body weight. In various embodiments, the TGF-β ligand trap is administered to the subject 1-7 times per week or once weekly, or once every two, three or four weeks. In various embodiments, the TGF-β ligand trap is administered to the subject for 1-5 days, 1-5 weeks, 1-5 months, or 1-5 years.

Although certain exemplar routes of administration are provided according to the invention, any suitable route of administration of a TGF-β ligand trap may be adapted, and therefore the routes of administration described herein are not intended to be limiting. Routes of administration may including but are not limited to, intravenous, oral, buccal, intranasal, inhalation, topical application to a mucosal membrane or injection, including intradermal, intrathecal, intracisternal, intralesional or any other type of injection. Administration can be effected continuously or intermittently and will vary with the subject and the condition to be treated. One of skill in the art would readily appreciate that the various routes of administration described herein would allow for a TGF-β ligand trap or compositions to be delivered on, in, or near the pulmonary disease locations or targeted cells. One of skill in the art would also readily appreciate that various routes of administration described herein will allow for a TGF-β ligand trap and compositions described herein to be delivered to a region in the vicinity of diseased tissues, organs, or individual cells to be treated. "In the vicinity" can include any tissue or bodily fluid in the subject that is in sufficiently close proximity to or in sufficient communication with diseased tissues, organs, or individual cells such that at least a portion of the TGF-β ligand trap or compositions administered to the subject reach their intended targets and exert their therapeutic effects.

Pharmaceutical Compositions

In various embodiments, the present invention provides a pharmaceutical composition that includes a TGF-β ligand trap described herein. In various embodiments, the pharmaceutical composition is formulated for modified release, sustained release, or controlled release, or a combination thereof. In various embodiments, the pharmaceutical composition is formulated for oral, via inhalation, nasal, sublingual, buccal, subcutaneous, intradermal, intramuscular, intravenous, intraperitoneal, or parenteral administration.

In various embodiments, the pharmaceutical composition further includes at least one pharmaceutically acceptable excipient. Examples of excipients include but are not limited to starches, sugars, microcrystalline cellulose, diluents, granulating agents, lubricants, binders, disintegrating agents, wetting agents, emulsifiers, coloring agents, release agents, coating agents, sweetening agents, flavoring agents, perfuming agents, preservatives, antioxidants, plasticizers, gelling agents, thickeners, hardeners, setting agents, suspending agents, surfactants, humectants, carriers, stabilizers, and combinations thereof.

In various embodiments, the pharmaceutical composition further includes at least one pharmaceutically acceptable carrier. Pharmaceutically acceptable carriers are well known in the art and include aqueous solutions such as physiologically buffered saline or other solvents or vehicles such as glycols, glycerol, vegetable oils (e.g., olive oil) or injectable organic esters. A pharmaceutically acceptable carrier can be used to administer the compositions of the invention to a cell in vitro or to a subject in vivo. A pharmaceutically acceptable carrier can contain a physiologically acceptable compound that acts, for example, to stabilize the composition or to increase the absorption of the agent. A physiologically acceptable compound can include, for example, carbohydrates, such as glucose, sucrose or dextrans, antioxidants, such as ascorbic acid or glutathione, chelating agents, low molecular weight proteins or other stabilizers or excipients. Other physiologically acceptable compounds include wetting agents, emulsifying agents, dispersing agents or preservatives, which are particularly useful for preventing the growth or action of microorganisms. Various preservatives are well known and include, for example, phenol and ascorbic acid. One skilled in the art would know that the choice of a pharmaceutically acceptable carrier, including a physiologically acceptable compound, depends, for example, on the route of administration of the polypeptide. For example, a physiologically acceptable compound such as aluminum monosterate or gelatin is particularly useful as a delaying agent, which prolongs the rate of absorption of a pharmaceutical composition administered to a subject. Further examples of carriers, stabilizers or adjutants can be found in Martin, Remington's Pharm. Sci., 15th Ed. (Mack Publ. Co., Easton, 1975), incorporated herein by reference. Other examples of carriers include, but are not limited to, a nanoparticle-based carrier (e.g. a polymer N-(2-hydorxylpropyl)methacrylamide (HPMA), glutamic acid, PEG, dextran) and a nanocarrier (e.g., nanoshell, liposome, nanoliposome).

Treatment Methods

In various embodiments, the present invention provides a method of treating, preventing, or reducing the progression rate of pulmonary hypertension (PH) in a subject. In some embodiments, the method includes administering a therapeutically effective amount of a TGF-β ligand trap to the subject, thereby treating, preventing, or reducing the progression rate of PH in the subject. In some embodiments, the method can further include mixing a pharmaceutically acceptable carrier with the TGF-β ligand trap prior to administering a therapeutically effective amount of the TGF-β ligand trap to the subject. Pulmonary arterial hypertension is a type of pulmonary hypertension that may be particularly amenable to treatment with a TGF-β ligand trap. Accordingly, in some embodiments, the method includes administering a therapeutically effective amount of a TGF-β ligand trap to the subject, thereby treating, preventing, or reducing the progression rate of pulmonary arterial hypertension in the subject, including any of the following subcategories of pulmonary arterial hypertension. Pulmonary arterial hypertension can arise secondary to other conditions or a as a primary or idiopathic pulmonary arterial hypertension. Of particular interest, certain types of familial pulmonary arterial hypertension are associated with decreased expression or function of the bone morphogenetic protein receptor type II (BMPRII), which is thought to result in excessive signaling by TGF-β.

Pulmonary hypertension can be of five major types, thus a series of tests is performed to distinguish pulmonary arterial hypertension from venous, hypoxic, thromboembolic, or miscellaneous varieties. These generally include pulmonary function tests; blood tests to exclude HIV, autoimmune diseases, and liver disease; electrocardiography (ECG); arterial blood gas measurements; X-rays of the chest (followed by high-resolution CT scanning if interstitial lung disease is suspected); and ventilation-perfusion or V/Q scanning to exclude chronic thromboembolic pulmonary hypertension. Diagnosis of PAH requires the presence of pulmonary hypertension. Although pulmonary arterial pressure can be estimated on the basis of echocardiography, pressure measurements with a Swan-Ganz catheter through the right side of the heart provides the most definite assessment for diagnosis.

On of skilled in the art is well versed in monitoring improvement in pulmonary hypertension, e.g. Clinical improvement is often measured by a "six-minute walk test", i.e. the distance a patient can walk in six minutes. Stability and improvement in this measurement correlate with better survival. Blood BNP level is also being used now to follow progress of patients with pulmonary hypertension. Improvement of symptoms can also be monitored by assaying arterial pressure. For example, normal pulmonary arterial pressure in a person living at sea level has a mean value of 8-20 mm Hg (1066-2666 Pa) at rest. Pulmonary hypertension is present when mean pulmonary artery pressure exceeds 25 mm Hg (3300 Pa) at rest. Mean pulmonary artery pressure (mPAP) should not be confused with systolic pulmonary artery pressure (sPAP), which is often reported on echocardiogram reports. A systolic pressure of 40 mm Hg typically implies a mean pressure of more than 25 mm Hg. Roughly, mPAP=0.61·sPAP+2.

In various embodiments, the present invention provides a method of treating, preventing, or reducing the progression rate of pulmonary vascular remodeling in a subject. In some embodiments, the method includes administering a therapeutically effective amount of a TGF-β ligand trap to the subject, thereby treating, preventing, or reducing the progression rate of pulmonary vascular remodeling in the subject. In some embodiments, the method can further include mixing a pharmaceutically acceptable carrier with the TGF-β ligand trap prior to administering a therapeutically effective amount of the TGF-β ligand trap to the subject.

In various embodiments, the present invention provides a method of treating, preventing, or reducing the progression rate of vascular remodeling in the heart of a subject. In some embodiments, the method can further include mixing a pharmaceutically acceptable carrier with the TGF-β ligand trap prior to administering a therapeutically effective amount of the TGF-β ligand trap to the subject. In certain embodiments, the methods of the invention reduce mitral valve degeneration, or e.g. mitral valve prolapse. Beneficial effects can be monitored by echocardiography.

In various embodiments, the present invention provides a method of treating, preventing, or reducing the progression rate of pulmonary fibrosis in a subject. In certain embodiments, the method includes administering a therapeutically effective amount of a TGF-β ligand trap to the subject, thereby treating, preventing, or reducing the progression rate of pulmonary fibrosis in the subject. In various embodiments, the method can further include mixing a pharmaceutically acceptable carrier with the TGF-β ligand trap prior to administering a therapeutically effective amount of the TGF-β ligand trap to the subject.

In various embodiments, the present invention provides a method of treating, preventing, or reducing the progression rate of right ventricular hypertrophy in a subject. In various embodiments, the method includes administering a therapeutically effective amount of a TGF-β ligand trap to the subject, thereby treating, preventing, or reducing the progression rate of right ventricular hypertrophy in the subject. In some embodiments, the method can further include mixing a pharmaceutically acceptable carrier with the TGF-β ligand trap prior to administering a therapeutically effective amount of the TGF-β ligand trap to the subject.

In various embodiments, the present invention provides a method of treating, preventing, or reducing the progression rate of a pulmonary disease associated with excessive TGF-β signaling in a subject. In some embodiments, the method includes administering a therapeutically effective amount of a TGF-β ligand trap to the subject, thereby treating, preventing, or reducing the progression rate of the disease in the subject. In some embodiments, the method can further include mixing a pharmaceutically acceptable carrier with the TGF-β ligand trap prior to administering a therapeutically effective amount of the TGF-β ligand trap to the subject.

In various embodiments, the TGF-β can be TGF-β1, TGF-β3, or a combination thereof.

In various embodiments, the present invention provides a method of treating, preventing, or reducing the progression rate of a pulmonary disease associated with excessive GDF15 signaling in a subject. In some embodiments, the method includes administering a therapeutically effective amount of a TGF-β ligand trap to the subject, thereby treating, preventing, or reducing the progression rate of the disease in the subject. In some embodiments, the method can further include mixing a pharmaceutically acceptable carrier with the TGF-β ligand trap prior to administering a therapeutically effective amount of the TGF-β ligand trap to the subject.

In various embodiments, the present invention provides a method of treating, preventing, or reducing the progression rate of a pulmonary disease associated with excessive PAI-1 signaling in a subject. In some embodiments, the method includes administering a therapeutically effective amount of a TGF-β ligand trap to the subject, thereby treating, preventing, or reducing the progression rate of the disease in the subject. In some embodiments, the method can further include mixing a pharmaceutically acceptable carrier with the TGF-β ligand trap prior to administering a therapeutically effective amount of the TGF-β ligand trap to the subject.

In various embodiments, the present invention provides a method of reducing right ventricular systolic pressure in a subject. In some embodiments, the method includes administering a therapeutically effective amount of a TGF-β ligand trap to the subject, thereby reducing right ventricular systolic pressure in the subject. In certain embodiments, the method can further include mixing a pharmaceutically acceptable carrier with the TGF-β ligand trap prior to administering a therapeutically effective amount of the TGF-β ligand trap to the subject.

In various embodiments, the subjects in the examples described above are mammals. In some embodiments, the subject is a human, monkey, ape, dog, cat, cow, horse, goat, sheep, pig, rabbit, mouse, or rat. In various embodiments, the TGF-β is TGF-β1, TGF-β3, or a combination thereof.

In various embodiments, the amount of TGF-β ligand trap administered to the subject is 0.05 mg to 50 mg/kg of body weight, and optionally 1.0 mg to 10 mg/kg of body weight or 0.3 mg to 3.0 mg/kg of body weight. In various embodiments, the TGF-β ligand trap is administered to the subject 1-7 times per week or once weekly, or once every two, three or four weeks. In various embodiments, the TGF-β ligand trap is administered to the subject for 1-5 days, 1-5 weeks, 1-5 months, or 1-5 years. TGF-β ligand trap may be administered by any route used for protein therapeutics, including but not limited to subcutaneous, intravenous or intramuscular administration.

As indicated above, in various embodiments, the TGF-β ligand trap is administered to the subject orally, via inhalation, nasally, sublingually, buccally, subcutaneously, intradermally, intramuscularly, intravenously, intraperitoneally, or parenterally. In various embodiments, the TGF-β ligand trap is administered before, during, or after the subject develops a disease condition, including but not limited to pulmonary hypertension, pulmonary vascular remodeling, pulmonary fibrosis, right ventricular hypertrophy, pulmonary diseases associated with excessive TGF-β signaling, pulmonary diseases associated with excessive GDF15 signaling, and pulmonary diseases associated with excessive PAI-1 signaling.

In various embodiments, the TGF-β ligand trap is part of a pharmaceutical composition. In various embodiments, the pharmaceutical composition is formulated for modified release, sustained release, or controlled release, or a combination thereof. In various embodiments, the pharmaceutical composition is formulated for oral, via inhalation, nasal, sublingual, buccal, subcutaneous, intradermal, intramuscular, intravenous, intraperitoneal, or parenteral administration.

In various embodiments, the pharmaceutical composition further includes at least one pharmaceutically acceptable excipient. Examples of excipients include but are not limited to starches, sugars, microcrystalline cellulose, diluents, granulating agents, lubricants, binders, disintegrating agents, wetting agents, emulsifiers, coloring agents, release agents, coating agents, sweetening agents, flavoring agents, perfuming agents, preservatives, antioxidants, plasticizers, gelling agents, thickeners, hardeners, setting agents, suspending agents, surfactants, humectants, carriers, stabilizers, and combinations thereof.

In some embodiments of the present invention may be defined in any of the following numbered paragraphs:

Paragraph 1. A method of treating, preventing, or reducing the progression rate of pulmonary hypertension (PH) in a subject, comprising: administering a therapeutically effective amount of a TGF-β ligand trap to the subject, thereby treating, preventing, or reducing the progression rate of PH in the subject.

Paragraph 2. The method of paragraph 1, wherein PH is mediated by excessive TGF-β signaling.

Paragraph 3. The method of any of paragraphs 1-2, wherein the subject is a human.

Paragraph 4. The method of any of paragraphs 1-3, wherein the TGF-β ligand trap comprises 1) a TGF-β ligand binding domain of a TGF receptor and 2) a Fc domain of an immunoglobulin.

Paragraph 5. The method of paragraph 4, wherein the TGF-β ligand trap further comprises a linker between the TGF-β ligand binding domain of a TGF receptor and the Fc domain.

Paragraph 6. The of any of paragraphs 1-5, wherein the TGF-β ligand trap is a soluble recombinant TGF-β type II receptor Fc-fusion protein (TGFBRII-Fc).

Paragraph 7. The method of any of paragraphs 1-6, wherein the TGFBRII-Fc consists of the sequence set forth in SEQ ID NO:1 or a variant thereof.

Paragraph 8. The method of any of paragraphs 1-6, wherein the TGFBRII-Fc comprises the sequence set forth in SEQ ID NO:1 or a variant thereof.

Paragraph 9. The method of any of paragraphs 1-6, wherein the TGFBRII-Fc comprises one or more biologically active portions of the sequence set forth in SEQ ID NO:1.

Paragraph 10. The method of any of paragraphs 1-6, wherein the TGFBRII-Fc is encoded by a nucleic acid comprising a nucleotide sequence set forth in SEQ ID NO:2 or a degenerate variant thereof.

Paragraph 11. The method of any of paragraphs 1-10, wherein the amount of TGF-β ligand trap administered to the subject is 0.1-10 mg/kg of body weight.

Paragraph 12. The method of any of paragraphs 1-11, wherein the TGF-β ligand trap is administered to the subject 1-7 times per month.

Paragraph 13. The method of any of paragraphs 1-12, wherein the TGF-β ligand trap is administered to the subject for 1-5 days, 1-5 weeks, 1-5 months, or 1-5 years.

Paragraph 14. The method of any of paragraphs 1-13, wherein the TGF-β ligand trap is administered to the subject orally, via inhalation, nasally, sublingually, buccally, subcutaneously, intradermally, intramuscularly, intravenously, intraperitoneally, or parenterally.

Paragraph 15. The method of any of paragraphs 1-14, wherein the TGF-β ligand trap is administered before, during, or after the subject develops PH.

Paragraph 16. The method of any of paragraphs 1-15, further comprising mixing a pharmaceutically acceptable carrier with the TGF-β ligand trap prior to administering a therapeutically effective amount of the TGF-β ligand trap to the subject.

Paragraph 17. The method of any of paragraphs 1-16, wherein the TGF-β ligand trap is part of a pharmaceutical composition.

Paragraph 18. The method of paragraph 17, wherein the pharmaceutical composition is formulated for modified release, sustained release, or controlled release, or a combination thereof.

Paragraph 19. The method of paragraph 17, wherein the pharmaceutical composition is formulated for oral, via inhalation, nasal, sublingual, buccal, subcutaneous, intradermal, intramuscular, intravenous, intraperitoneal, or parenteral administration.

Paragraph 20. The method of paragraph 17, wherein the pharmaceutical composition further comprises at least one pharmaceutically acceptable excipient.

Paragraph 21. The method of paragraph 17, wherein the pharmaceutical composition further comprises at least one pharmaceutically acceptable carrier.

Paragraph 22. A method of treating, preventing, or reducing the progression rate of pulmonary vascular remodeling in a subject, comprising: administering a therapeutically effective amount of a TGF-β ligand trap to the subject, thereby treating, preventing, or reducing the progression rate of pulmonary vascular remodeling in the subject.

Paragraph 23. A method of treating, preventing, or reducing the progression rate of pulmonary fibrosis in a subject, comprising: administering a therapeutically effective amount of a TGF-β ligand trap to the subject, thereby treating, preventing, or reducing the progression rate of pulmonary fibrosis in the subject.

Paragraph 24. The method of paragraph 23, using the TGF-β ligand trap of any of paragraphs 4-10.

Paragraph 25. A method of treating, preventing, or reducing the progression rate of right ventricular hypertrophy in a subject, comprising: administering a therapeutically effective amount of a TGF-β ligand trap to the subject, thereby treating, preventing, or reducing the progression rate of right ventricular hypertrophy in the subject.

Paragraph 26. The method of paragraph 25, using the TGF-β ligand trap of any of paragraphs 4-10.

Paragraph 27. A method of treating, preventing, or reducing the progression rate of a pulmonary disease associated with excessive TGF-β signaling in a subject, comprising: administering a therapeutically effective amount of a TGF-β ligand trap to the subject, thereby treating, preventing, or reducing the progression rate of the disease in the subject.

Paragraph 28. The method of paragraph 27, using the TGF-β ligand trap of any of paragraphs 4-10.

Paragraph 29. The method of any of paragraphs 1-28, wherein the TGF-β is TGF-β1, TGF-β3, or a combination thereof.

Paragraph 30. A method of treating, preventing, or reducing the progression rate of a pulmonary disease associated with excessive GDF15 signaling in a subject, comprising: administering a therapeutically effective amount of a TGF-β ligand trap to the subject, thereby treating, preventing, or reducing the progression rate of the disease in the subject.

Paragraph 31. The method of paragraph 30, using the TGF-β ligand trap of any of paragraphs 4-10.

Paragraph 32. A method of treating, preventing, or reducing the progression rate of a pulmonary disease associated with excessive PAI-1 signaling in a subject, comprising: administering a therapeutically effective amount of a TGF-β ligand trap to the subject, thereby treating, preventing, or reducing the progression rate of the disease in the subject.

Paragraph 33. The method of paragraph 32, using the TGF-β ligand trap of any of paragraphs 4-10

Paragraph 34. A method of reducing right ventricular systolic pressure in a subject, comprising: administering a therapeutically effective amount of a TGF-β ligand trap to the subject, thereby reducing right ventricular systolic pressure in the subject.

Paragraph 35. The method of paragraph 34, using the TGF-β ligand trap of any of paragraphs 4-10.

EXAMPLES

The following examples are provided to better illustrate the claimed invention and are not to be interpreted as limiting the scope of the invention. To the extent that specific materials are mentioned, it is merely for purposes of illustration and is not intended to limit the invention. One skilled in the art may develop equivalent means or reactants without the exercise of inventive capacity and without departing from the scope of the invention.

Example 1

Additional Background and Brief Summary of Results

As indicated above, Transforming Growth Factor-(TGF-β) ligands coordinate important processes in development, and regulate fibrosis and tissue remodeling in disease. An excess of TGF-β signaling has been implicated in the arterial remodeling of pulmonary hypertension (PH), based in part on the ability of TGFβ type I receptor (ALK5) kinase inhibitors to improve experimental PH in animal models. However, clinical deployment of ALK5 inhibitors has been limited by cardiovascular toxicity. The experiments and results disclosed herein demonstrate that a soluble recombinant TGFβ type II receptor Fc-fusion protein (TGFBRII-Fc) inhibits TGFβ signaling in rat monocrotaline (MCT)-induced PH. When administered prophylactically following MCT, TGFBRII-Fc treatment reduced right ventricular systolic pressure, right ventricular hypertrophy, and attenuated pulmonary vascular remodeling. Elevated mRNA levels of TGFβ transcriptional target PAI-1 in lungs of MCT rats were corrected by TGFBRII-Fc, consistent with attenuating of TGFβ signaling. When administered 2.5 weeks after MCT, TGFβRII-Fc partially rescued established PH with a trend towards improved survival at 5 weeks. Of note, no cardiac structural or valvular abnormalities were found in association with treatment with TGFBRII-Fc at any dose. Collectively, the data disclosed herein supports the conclusion that a TGFβ ligand trap could be an effective and acceptably safe strategy for correcting TGFβ-mediated pulmonary vascular remodeling and PH.

Example 2

TABLE 1

Non-limiting Exemplar TGFβ Ligand Binding Domains

| TGFβ Receptor | Ligand-Binding Domains | SEQ ID NO: |
|---|---|---|
| Human TGFβ receptor type II | QLCKFCDVRFSTCDNQKSCMSNCSITSICEKPQEVCVA VWRKNDENITLETVCHDPKLPYHDFILEDAASPKCIM KEKKKPGETFFMCSCSSDECNDNIIF | 3 |
| Human TGFβ receptor type IIb | QLCKFCDVRFSTCDNQKSCMSNCSITSICEKPQEVCVA VWRKNDENITLETVCHDPKLPYHDFILEDAASPKCIM KEKKKPGETFFMCSCSSDECNDNIIF | 4 |
| Human TGFβ receptor type I | ALQCFCHLCTKDNFTCVTDGLCFVSVTETTDKVIHNS MCIAEIDLIPRDRPFVCAPSSKTGSVTTTYCCNQDHCN KIEL | 5 |

Example 3

TABLE 2

Non-limiting Exemplar Linkers

| Linker | SEQ ID NO: |
|---|---|
| COOH-IPPHVQKSVNNDMIVTDNNGAVKFP-NH2 | 6 |
| COOH-SEEYNTSNPD-NH2 | 7 |
| COOH-IPPHVQKSDVEMEAQKDEIICPSCNRTAHPLRHINNDMIVTDNNGAVKFP-NH2 | 8 |
| COOH-AALLPGAT-NH2 | 9 |
| COOH-PTTVKSSPGLGPVE-NH2 | 10 |
| COOH-AILGRSE-NH2 | 11 |
| COOH-EMEVTQPTSNPVTPKPPYYNI-NH2 | 12 |
| COOH-SGRGEAET-NH2 | 13 |

TABLE 2-continued

Non-limiting Exemplar Linkers

| Linker | SEQ ID NO: |
| --- | --- |
| COOH-EAGGPEVTYEPPPTAPT-NH2 | 14 |
| COOH-QNLDSMLHGTGMKSDSDQKKSENGVTLAPED-NH2 | 15 |
| COOH-PVVIGPFFDGSIR-NH2 | 16 |
| COOH-QLCKFCDVRFSTCDNQKSCMSNCSITSICEKPQEVCVAVWRKNDENITLETVCHDPKLPYHDFILEDAASPKCIMKEKKKPGETFFMCSCSSDECNDNIIF-NH2 | 17 |
| COOH-QLCKFCDVRFSTCDNQKSCMSNCSITSICEKPQEVCVAVWRKNDENITLETVCHDPKLPYHDFILEDAASPKCIMKEKKKPGETFFMCSCSSDECNDNIIF-NH2 | 18 |
| COOH-ALQCFCHLCTKDNFTCVTDGLCFVSVTETTDKVIHNSMCIAEIDLIPRDRPFVCAPSSKTGSVTTTYCCNQDHCNKIEL-NH2 | 19 |
| COOH-TQECLFFNANWEKDRTNQTGVEPCYGDKDKRRHCFATWKNISGSIEIVKQGCWLDDINCYDRTDCVEKKDSPEVYFCCCEGNMCNEKFSYFP-NH2 | 20 |
| COOH-RECIYYNANWELERTNQSGLERCEGEQDKRLHCYASWRNSSGTIELVKKGCWLDDFNCYDRQECVATEENPQVYFCCCEGNFCNERFTHLPEAGGPEVTYEPPPTAPT-NH2 | 21 |
| COOH-TLPFLKCYCSGHCPDDAINNTCITNGHCFAIIEEDDQGETTLASGCMKYEGSDFQCKDSPKAQLRRTIECCRTNLCNQYLQPTLPPVVIGPFFDGSIR-NH2 | 22 |
| COOH-SEEYNTSNPDIPPHVQKSVNNDMIVTDNNGAVKFP-NH2 | 23 |
| COOH-SEEYNTSNPDIPPHVQKSDVEMEAQKDEIICPSCNRTAHPLRHINNDMIVTDNNGAVKFP-NH2 | 24 |
| COOH-EAGGPEVTYEPPPTAPTSGRGEAET-NH2 | 25 |
| COOH-PVVIGPFFDGSIRQNLDSMLHGTGMKSDSDQKKSENGVTLAPED-NH2 | 26 |
| COOH-PVVIGPFFDGSIRGNLDSMLHGTGMKSDSDQKKSENGVTLAPED-NH2 | 27 |
| COOH-SEEYNTSNPDGPPHVQKSVNNDMIVTDNNGAVKFP-NH2 | 28 |
| COOH-EAGGPEVTGEPPPTAPTSGRGEAET-NH2 | 29 |
| COOH-SEEYNTSNPDGGRHVQKSDVEMEAQKDEIICPSCNRTAHPLRHINNDMIVTDNNGAVKFP-NH2 | 30 |
| COOH-SEEYNTSNPDGGPHVQKSVNNDMIVTDNNGAVKFP-NH2 | 31 |
| COOH-SEEYNTSNPDGGRHVQKSVNNDMIVTDNNGAVKFP-NH2- | 32 |
| COOH-SEEYNTSNPSGGGSGGGSGGGMEAQKDEIICPSCNRTAHPLRHINNDMIVTDNNGAVKFP-NH2 | 33 |
| COOH-SEEYNTSNPSGGGSGGKSVNNDMIVTDNNGAVKFP-NH2 | 34 |
| COOH-SEEYNTSNPSGGGSGGGSGGGDMIVTDNNGAVKFP-NH2 | 35 |
| COOH-SEEYNTSNPDIPPHVQKSGGGSGGGSGGGSGGGSGGGSGGGSGGNNDMIVTDNNGAVKFP-NH2 | 36 |

TABLE 2-continued

Non-limiting Exemplar Linkers

| Linker | SEQ ID NO: |
|---|---|
| COOH-SEEYNTSNPDGGGSGGGSGGGSGGGSGGGSGGGSGGGSGGGSGGNNDMIVTDNNGAVKFP-NH2 | 37 |
| COOH-SEEYNTSNPDIPPHVQKSVNNDMIVTDNNGAVKFP-NH2 | 38 |
| COOH-SEEYNTSNPDIPPHVQKSVNNDMIPPHVQKSVNNDMIVIDNNGAVKFP-NH2 | 39 |
| COOH-SEEYNTSNPPHVQKSVNNDMIVTDNNGAVKFP-NH2 | 40 |
| COOH-SEEYNTSNPDGGGGGGGGIPPHVQKSVNNDMIVIDNNGAVKFP-NH2 | 41 |
| COOH-SEEYNTSNPDGGGSGGGSGGGSIPPHVQKSVNNDMIVTDNNGAVKFP-NH2 | 42 |
| COOH-SEEYNTSNPDIPPHVQKSDVEMEAQKDEIICPSCNRTAHPLRHINNDMIVTDNNGAVKFP-NH2 | 43 |
| COOH-SEEYNTSNPDIPPHVQKSDVEMEAQKDERTAHPLRHINNDMIVTDNNGAVKFP-NH2 | 44 |
| COOH-EAGGPEVTYEPPPTAPTSGRGEAET-NH2 | 45 |
| COOH-EAGGPEVTYEPPPTAPTGGGGGGGGGSGRGEAET-NH2 | 46 |
| COOH-PVVIGPFFDGSIRQNLDSMLHGTGMKSDSDQKKSENGVTLAPED-NH2 | 47 |
| COOH-PVVIGPDGSIRQNLDSHGTGMKSDSDQKKSENGVTLAPED-NH2 | 48 |

Also contemplated are nucleic acid sequences encoding each of the above linkers and binding domains.

Example 4

Materials and Methods

Rat Model of PAH

Male Sprague-Dawley rats (6-8 weeks old, weight 150 to 170 g) were purchased from Charles River Laboratory. All protocols and surgical procedures were approved by the local animal care committee. Animals were housed at 24° C. in a 12-hour light-dark cycle. Food and water were accessible ad libitum. To induce PAH, rats received a single subcutaneous injection of monocrotaline (MCT, 40 mg/kg). Mortality and total number of rats included in the present study are summarized in Table 3.

TABLE 3

Figure 3:
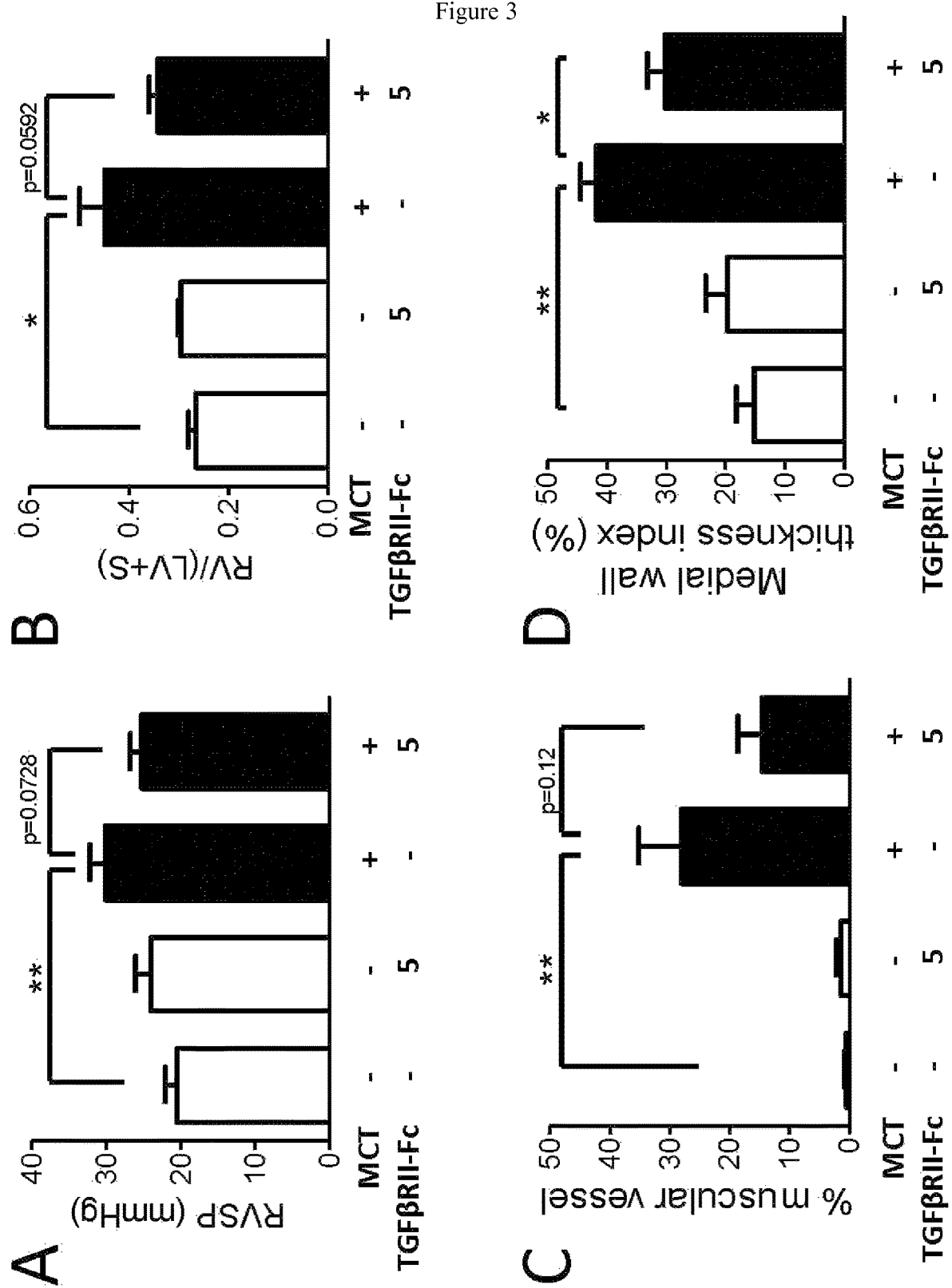
FIGS. 3A to 3D are graphs that demonstrate, in accordance with an embodiment of the invention, low dose TGFBRII-Fc treatment causes a trend towards reduced right ventricular systolic pressure (RVSP), a trend towards reduced right ventricular hypertrophy, and significantly reduced pulmonary vascular remodeling. Three weeks following treatment with MCT with or without TGFBRII-Fc (5 mg/kg, twice weekly), rats were analyzed in a blinded fashion by catheterization under anesthesia with pentobarbital and intratracheal intubation to determine RVSP (FIG. 3A), systemic arterial pressures (not shown), and euthanized. The degree of RVH was assessed in a blinded fashion based on measurement of Fulton's ratio (RV/(LV+S) (FIG. 3B). Values are represented as mean±SEM, n=6-8, *p<0.05 and **p<0.01 compared to control rats. Lung tissue sections were stained with alpha smooth muscle actin and von willebrand factor to identify vascular smooth muscle vessels and endothelium, respectively. Muscularization of distal intra-acinar vessels (10-50 µm diameter) was quantified, and the percentage of nonmuscular, partially muscularized, and fully (circumferentially) muscularized vessels was calculated (FIG. 3C). Medial wall thickness was calculated for all fully muscularized intra-acinar vessels (10-50 µm diameter, FIG. 3D). Wall thickness index was calculated as: index= (external diameter−internal diameter)/external diameter× 100. TGFBRII-Fc treatment (5 mg/kg, twice weekly) caused a trend towards reduced percentage of fully muscularized vessel and significantly reduced medial wall thickness index. Values are represented as mean±SEM, n=100-150 vessels per treatment group from 6-8 rats each, p values as shown.

| | Experimental group | Starting n number | Data excluded due to mortality or low heart rate (<350 bpm) during right ventricular catheterization | Final n number included |
|---|---|---|---|---|
| FIG. 3 | Control | 6 | 0 | 6 |
| | TGFBRII-Fc | 6 | 0 | 6 |

TABLE 3-continued

Figure 4:
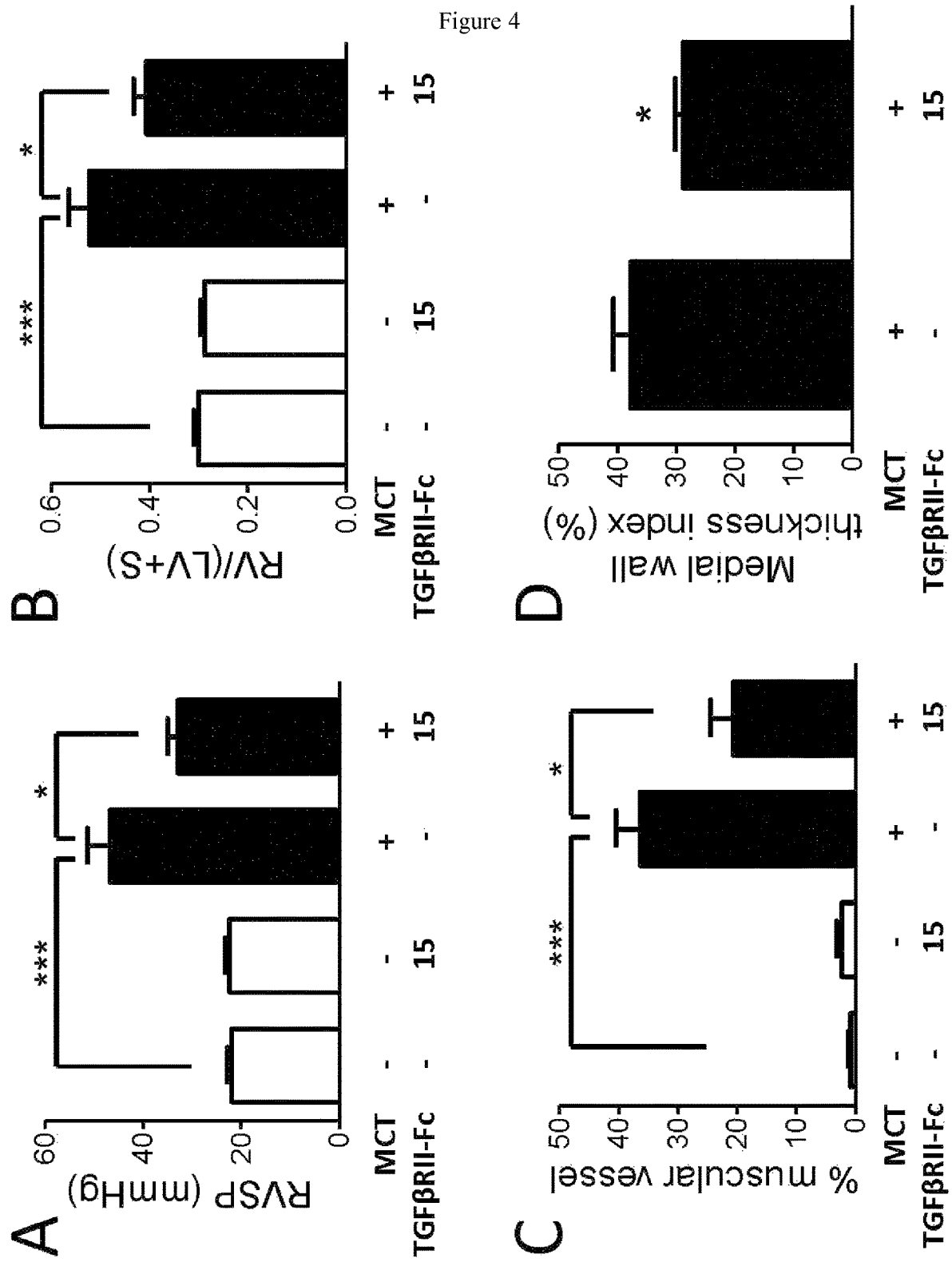
FIGS. 4A to 4D show graphs that demonstrate, in accordance with an embodiment of the invention, high dose TGFBRII-Fc treatment attenuates right ventricular systolic pressure (RVSP), right ventricular hypertrophy, and prevents pulmonary vascular remodeling. Three weeks following treatment with MCT with or without TGFBRII-Fc (15 mg/kg, twice weekly), rats were analyzed in a blinded fashion to determine RVSP (FIG. 4A). The degree of RVH was assessed in a blinded fashion based on measurement of Fulton's ratio (FIG. 4B). Values are represented as mean±SEM, n=6-8. Muscularization of distal intra-acinar vessels (10-50 μm diameter) was quantified (FIG. 4C). Medial wall thickness was calculated for all fully muscularized intra-acinar vessels (10-50 μm diameter, FIG. 4D). TGFBRII-Fc treatment (15 mg/kg twice weekly) significantly reduced the percentage of fully muscularized vessels, and reduced medial wall thickness index. Values are represented as mean±SEM, n=89-127 vessels per treatment group from 6-8 rats each, *p<0.05 and ***p<0.001 compared to control rats.
Figure 5:
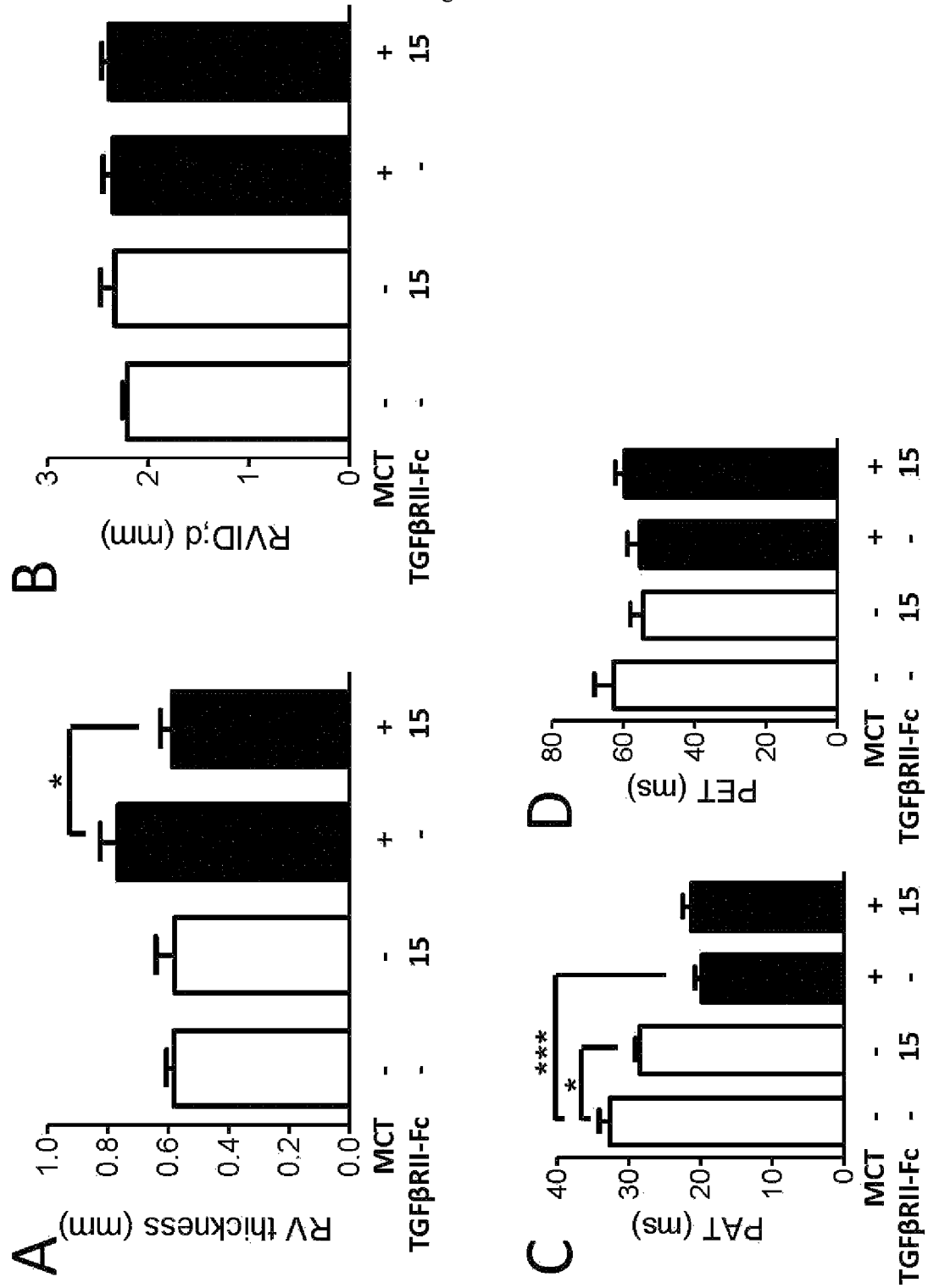
FIGS. 5A to 5D show graphs that demonstrate, in accordance with an embodiment of the invention, TGFBRII-Fc attenuates echocardiographic RV hypertrophy. Following MCT (40 mg/kg SC) treatment, rats were treated with vehicle or TGFBRII-Fc (15 mg/kg, twice per week) starting 24 hours after MCT. Two weeks following MCT, rats were analyzed under anesthesia with 1.5% isoflurane by small animal ultrasonography to measure right ventricular thickness and diastolic dimension (FIG. 5A & FIG. 5B), pulmonary flow acceleration time (PAT, FIG. 5C), and pulmonary ejection time (PET, FIG. 5D). Values are represented as mean±SEM, n=6-8, *p<0.05 and ***p<0.001 compared to control rats.
Figure 6:
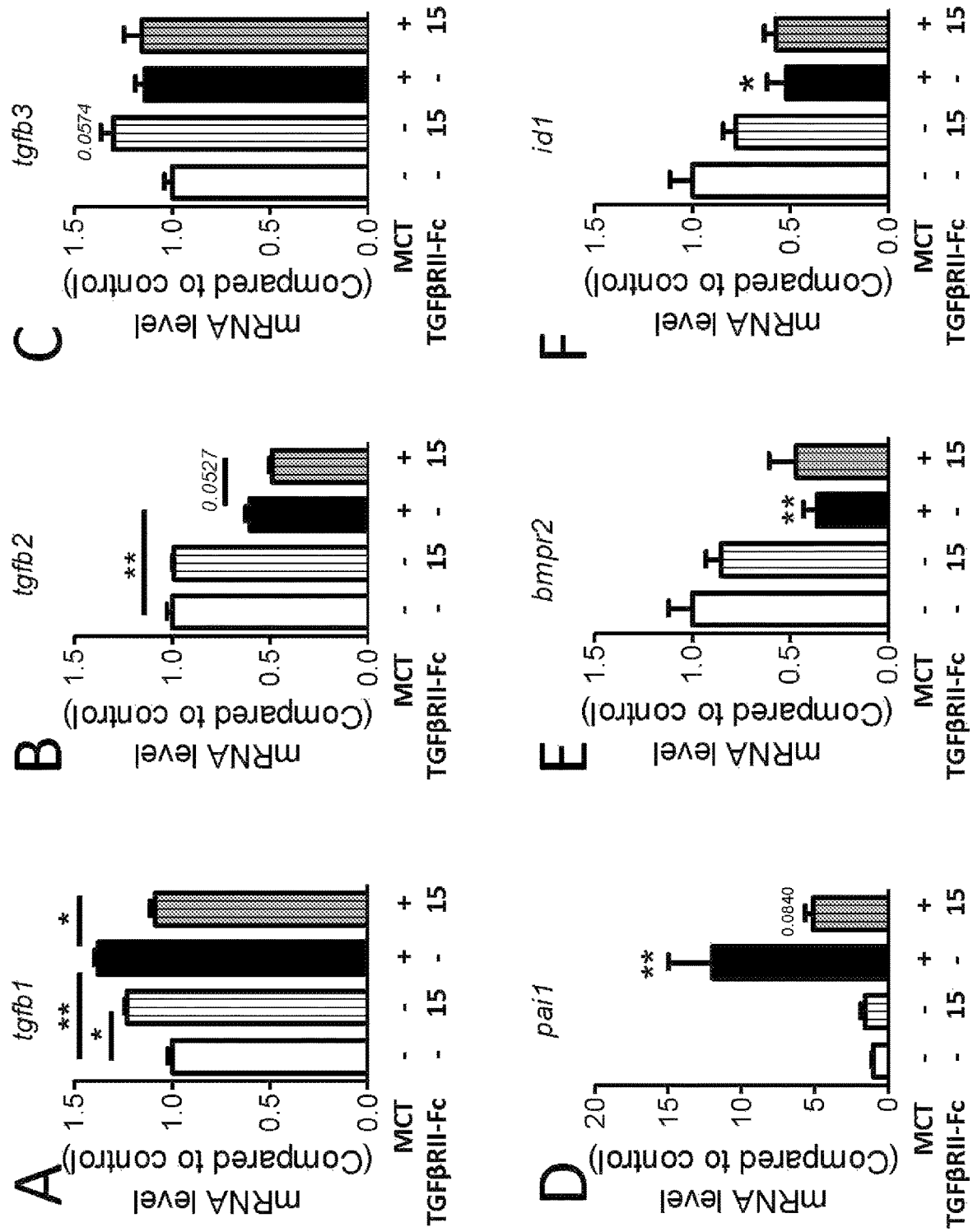
FIGS. 6A to 6F are graphs that demonstrate, in accordance with an embodiment of the invention, TGFBRII-Fc inhibited TGFβ-mediated transcription in PH lung tissues. MCT-induced PH was correlated with a modest increase in TGFβ1 and a significant decrease in TGFβ2 mRNA expression (FIG. 6A-FIG. 6C). Suppression of Bmpr2 and Id1 expression following MCT treatment was not affected by TGFBRII-Fc (15 mg/kg twice weekly, FIG. 6D-FIG. 6E), whereas treatment with TGFBRII-Fc resulted in significant decreases in TGFβ1 and its transcriptional target PAI-1 (FIG. 6F). Values are represented as mean±SEM, n=3-5, *p<0.05 and **p<0.01 compared to control.
Figure 7:
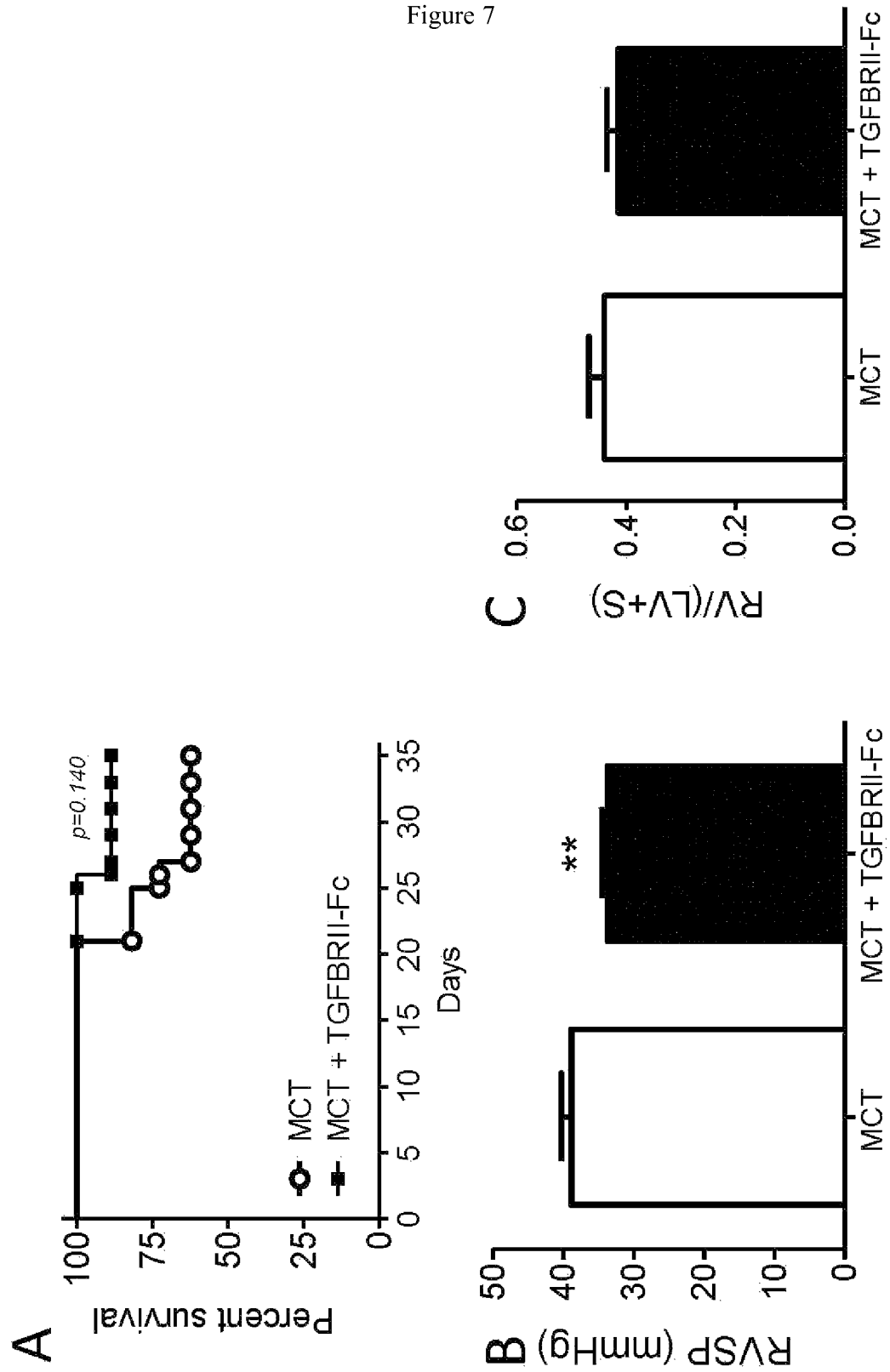
FIGS. 7A to 7C are graphs that demonstrate, in accordance with an embodiment of the invention, treatment with TGFBRII-Fc following establishment of PH is associated with partial rescue of PH and mortality in accordance with various embodiments of the present invention. After treatment with MCT (40 mg/kg SC), rats were treated in a delayed fashion starting on day 17 after the establishment of PH with TGFBRII-FC (15 mg/kg three times weekly). Kaplan-Meier analysis (FIG. 7A) revealed a trend towards improved survival in the TGFBRII-Fc-treated group as compared to rats treated with vehicle (n=12 per group, p=0.10). Among surviving animals at 35 days, there was significantly decreased RVSP among animals treated with TGFBRII-Fc (FIG. 7B). Among surviving animals, however, there was no significant difference in RVH (C). Values shown are mean±SEM, n=8-11 per group, **p<0.01 compared to control.

| | Experimental group | Starting n number | Data excluded due to mortality or low heart rate (<350 bpm) during right ventricular catheterization | Final n number included |
|---|---|---|---|---|
| | 5 mg/kg, twice per week MCT | 8 | 0 | 8 |
| | MCT + TGFBRII-Fc 5 mg/kg, twice per week | 8 | 0 | 8 |
| FIG. 4 and 5 | Control | 6 | 0 | 6 |
| | TGFBRII-Fc 15 mg/kg, twice per week | 6 | 0 | 6 |
| | MCT | 8 | 1 | 7 |
| | MCT + TGFBRII-Fc 15 mg/kg, twice per week | 8 | 0 | 8 |
| FIG. 7 | MCT | 12 | 4 | 8 |
| | MCT + TGFBRII-Fc 15 mg/kg, three time per week | 12 | 1 | 11 |

Drug Treatment

Prophylaxis protocol—At 24 hours after PAH induction, rats were randomized into TGFBRII-Fc (5 or 15 mg/kg, twice per week) or vehicle groups. Rats were treated for 21 days. At day 14, ventricular function and RV remodeling were examined by echocardiogram. At day 21, rats were subjected to hemodynamics and right ventricular hypertrophy measurements.

Rescue Protocol—

In another cohort, the ability of TGFBRII-Fc to reverse the progression of PAH was examined. At day 18, rats were injected with MCT and randomized for TGFBRII-Fc (15 mg/kg, three times per week) or vehicle. Hemodynamics and right ventricular hypertrophy (RVH) were examined on day 35.

Echocardiographic Assessment of LV and RV Function

At day 14 after PAH induction, rats were anesthetized with 1.5% isoflurane and held in a supine position. A VisualSonics small animal high-frequency ultrasound probe was used to detect pulmonary flow acceleration, right ventricular function and hypertrophy, and left ventricular function. Doppler across the mitral and tricuspid valves to determine if TGFBRII-Fc treatment induce any obvious regurgitation or lesions.

Hemodynamic and RVH Measurement

At specific time points, rats were anesthetized with pentobarbital and intubated through the trachea. Rats were mechanically ventilated using a rodent ventilator and hemodynamic assessment using a fluid-filled catheter through the right ventricular (RV) apex, as described previously (Megalou, A. J., Glava, C., Vilaeti, A. D., Oikonomidis, D. L., Baltogiannis, G. G., Papalois, A., Vlahos, A. P., and Kolettis, T. M. (2012) Pulm Circ 2, 461-469). Lungs were perfused with PBS and one right lobe was excised and snap frozen for RNA and protein extraction. Lungs were further perfused with 1% paraformaldehyde (PFA) into the pulmonary artery, followed by trachea for 1 minute. Left lobes were embedded in paraffin. To access degree of RVH, the heart was removed and the RV free wall dissected from the left ventricle plus septum (LV+S) and weighted separately. Degree of RVH was determined from the ration RV/(LV+S).

Quantification of Vascular Remodeling

To determine the degree of pulmonary vascular remodeling, lung tissue sections were stained with alpha smooth muscle actin and von willebrand factor. Muscularization of distal intra-acinar vessels (10-50 μm diameter) was quantified and percentage of nonmuscular, partially muscular, and fully muscular vessels was calculated.

Medial wall thickness was calculated for all fully muscularized intra-acinar vessels (10-50 μm diameter). Wall thickness index was calculated as: index=(external diameter−internal diameter)/external diameter×100.

Expression Studies

Frozen lung samples were homogenized and total RNA extraction using TRIZOL reagent performed as previously described (Long, L., Crosby, A., Yang, X., Southwood, M., Upton, P. D., Kim, D. K., and Morrell, N. W. (2009) Circulation 119, 566-576). Reverse transcription and quantitative PCR were performed as described (Long, L., Crosby, A., Yang, X., Southwood, M., Upton, P. D., Kim, D. K., and Morrell, N. W. (2009) Circulation 119, 566-576). The ratio of a specific gene to β-actin was calculated and expressed as fold change. Sequences of rat-specific are summarized in Table 4.

TABLE 4

| Gene of interest | Forward primer | SEQ ID NO: | Reverse primer | SEQ ID NO: |
|---|---|---|---|---|
| tgfb1 | TGAGTGGCTGTCTTTTGACG | 49 | TTCTCTGTGGAGCTGAAGCA | 50 |
| tgfb2 | CACGCCTCTCTTGTTTCCTC | 51 | TTTTCCAAGGGCAATGAAAG | 52 |
| tgfb3 | GAAGGCTGCACTCAGGAAAC | 53 | GCTGCTTGGCTATGTGTTCA | 54 |
| pai1 | CTTTATCCTGGGTCTCCCTG | 55 | TGATGCCTCCCTGACATACA | 56 |
| bmpr2 | AATAATCTGGGTAAGGCC | 57 | GCAGAACGAACGCAACCTATCA | 58 |
| id1 | TGGACGAACAGCAGGTGAACG | 59 | GCACTGATCTCGCCGTTCAGG | 60 |
| β-actin | TGTCACCAACTGGGACGATA | 61 | ACCCTCATAGATGGGCACAG | 62 |

Reagents

Monocrotaline was purchased from Oakwood Products, Inc. Recombinant human BMP4, TGFβ1, TGFβ2 and GDF15 were obtained from R&D Systems. Primary antibody specific to phospho-Smad 3 was purchased from Abcam, while other primary antibodies against phospho-Smad 2, phospho-Smad 1/5, and total Smad 3 were obtained from Cell Signaling.

Statistical Analysis

All the analysis of hemodynamic and RVH measurement and pulmonary vascular remodeling quantification were performed in a blinded manner. Data were presented as mean±SEM and compared between group using t test. $P<0.05$ was considered statistically significant.

Vascular Remodeling of Mitral Valve.

Figure 9A:
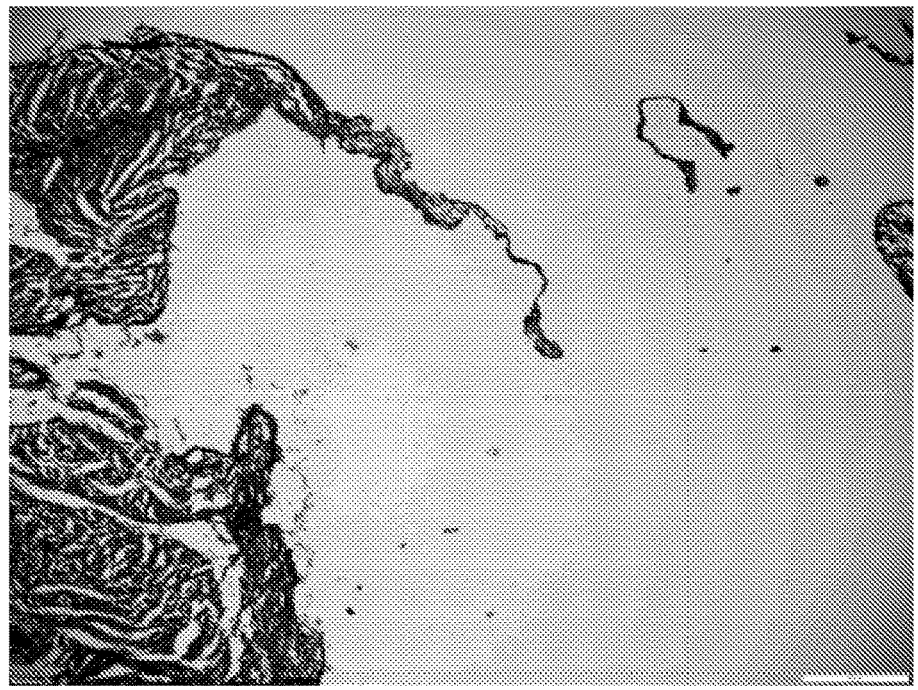
FIGS. 9A to 9B show tissue sections demonstrating the lack of mitral valve remodeling, degeneration or abnormalities in response to TGFBRII-Fc treatment.
Figure 9B:
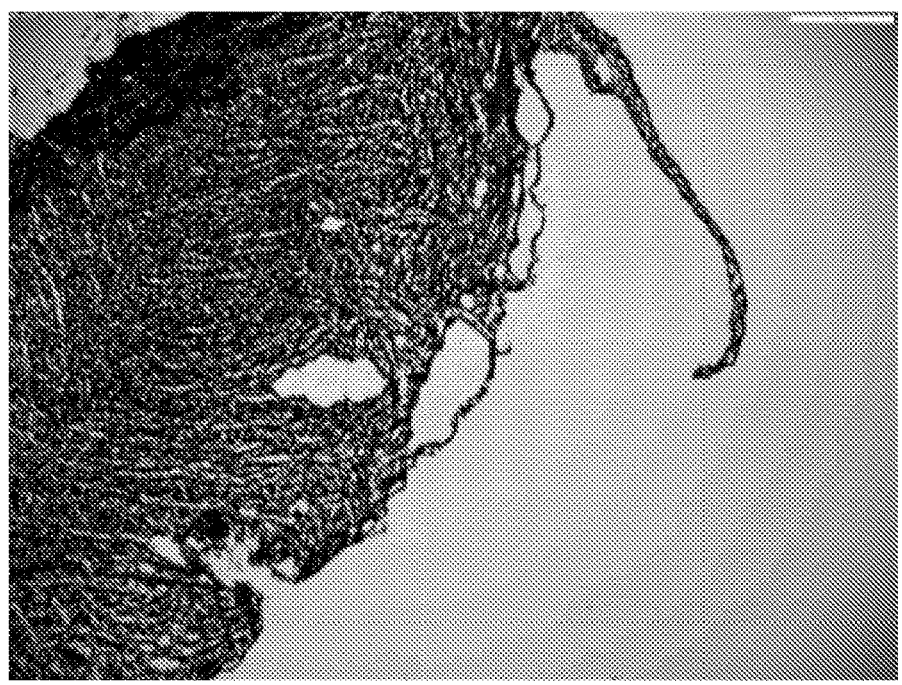

FIGS. 9A to 9B show heart tissue sections demonstrating the lack of mitral valve remodeling, degeneration or abnormalities in response to TGFBRII-Fc treatment. FIG. 9A control. FIG. 9B TGFBRII-Fc-treated.

The various methods and techniques described above provide a number of ways to carry out the application. Of course, it is to be understood that not necessarily all objectives or advantages described can be achieved in accordance with any particular embodiment described herein. Thus, for example, those skilled in the art will recognize that the methods can be performed in a manner that achieves or optimizes one advantage or group of advantages as taught herein without necessarily achieving other objectives or advantages as taught or suggested herein. A variety of alternatives are mentioned herein. It is to be understood that some preferred embodiments specifically include one, another, or several features, while others specifically exclude one, another, or several features, while still others mitigate a particular feature by inclusion of one, another, or several advantageous features.

Furthermore, the skilled artisan will recognize the applicability of various features from different embodiments. Similarly, the various elements, features and steps discussed above, as well as other known equivalents for each such element, feature or step, can be employed in various combinations by one of ordinary skill in this art to perform methods in accordance with the principles described herein. Among the various elements, features, and steps some will be specifically included and others specifically excluded in diverse embodiments.

Although the application has been disclosed in the context of certain embodiments and examples, it will be understood by those skilled in the art that the embodiments of the application extend beyond the specifically disclosed embodiments to other alternative embodiments and/or uses and modifications and equivalents thereof.

In some embodiments, the terms "a" and "an" and "the" and similar references used in the context of describing a particular embodiment of the application (especially in the context of certain of the following claims) can be construed to cover both the singular and the plural. The recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (for example, "such as") provided with respect to certain embodiments herein is intended merely to better illuminate the application and does not pose a limitation on the scope of the application otherwise claimed. No language in the specification should be construed as indicating any non-claimed element essential to the practice of the application.

Preferred embodiments of this application are described herein, including the best mode known to the inventors for carrying out the application. Variations on those preferred embodiments will become apparent to those of ordinary skill in the art upon reading the foregoing description. It is contemplated that skilled artisans can employ such variations as appropriate, and the application can be practiced otherwise than specifically described herein. Accordingly, many embodiments of this application include all modifications and equivalents of the subject matter recited in the claims appended hereto as permitted by applicable law. Moreover, any combination of the above-described elements in all possible variations thereof is encompassed by the application unless otherwise indicated herein or otherwise clearly contradicted by context.

All patents, patent applications, publications of patent applications, and other material, such as articles, books, specifications, publications, documents, things, and/or the like, referenced herein are hereby incorporated herein by this reference in their entirety for all purposes, excepting any prosecution file history associated with same, any of same that is inconsistent with or in conflict with the present document, or any of same that may have a limiting affect as to the broadest scope of the claims now or later associated with the present document. By way of example, should there be any inconsistency or conflict between the description, definition, and/or the use of a term associated with any of the incorporated material and that associated with the present document, the description, definition, and/or the use of the term in the present document shall prevail.

It is to be understood that the embodiments of the application disclosed herein are illustrative of the principles of the embodiments of the application. Other modifications that can be employed can be within the scope of the application. Thus, by way of example, but not of limitation, alternative configurations of the embodiments of the application can be utilized in accordance with the teachings herein. Accordingly, embodiments of the present application are not limited to that precisely as shown and described.

Various embodiments of the invention are described above in the Detailed Description. While these descriptions directly describe the above embodiments, it is understood that those skilled in the art may conceive modifications and/or variations to the specific embodiments shown and described herein. Any such modifications or variations that fall within the purview of this description are intended to be included therein as well. Unless specifically noted, it is the intention of the inventors that the words and phrases in the specification and claims be given the ordinary and accustomed meanings to those of ordinary skill in the applicable art(s).

The foregoing description of various embodiments of the invention known to the applicant at this time of filing the application has been presented and is intended for the purposes of illustration and description. The present description is not intended to be exhaustive nor limit the invention to the precise form disclosed and many modifications and variations are possible in the light of the above teachings. The embodiments described serve to explain the principles of the invention and its practical application and to enable others skilled in the art to utilize the invention in various embodiments and with various modifications as are suited to the particular use contemplated. Therefore, it is intended that the invention not be limited to the particular embodiments disclosed for carrying out the invention.

While particular embodiments of the present invention have been shown and described, it will be obvious to those skilled in the art that, based upon the teachings herein, changes and modifications may be made without departing from this invention and its broader aspects and, therefore, the appended claims are to encompass within their scope all such changes and modifications as are within the true spirit and scope of this invention. It will be understood by those within the art that, in general, terms used herein are generally intended as "open" terms (e.g., the term "including" should be interpreted as "including but not limited to," the term "having" should be interpreted as "having at least," the term "includes" should be interpreted as "includes but is not limited to," etc.)

What is claimed is:

1. A method of treating pulmonary hypertension (PH) in a subject, comprising: administering a therapeutically effective amount of a fusion protein comprising a transforming growth factor β (TGF-β) ligand binding domain of a TGF-β type II receptor and an Fc domain of an immunoglobulin to the subject, thereby treating PH in the subject, and wherein the fusion protein comprises an amino acid sequence set forth in SEQ ID NO: 1.

2. The method of claim 1, wherein PH is mediated by excessive TGF-β signaling.

3. The method of claim 1, wherein the subject is a human.

4. The method of claim 1, wherein the fusion protein comprises a linker between the TGF-β ligand binding domain and the Fc domain.

5. The method of claim 1, wherein the fusion protein consists of the sequence set forth in SEQ ID NO: 1.

6. The method of claim 1, wherein the amount of fusion protein administered to the subject is 0.1-10 mg/kg of body weight.

7. The method of claim 1, wherein the fusion protein is administered to the subject orally, via inhalation, nasally, sublingually, buccally, subcutaneously, intradermally, intramuscularly, intravenously, intraperitoneally, or parenterally.

8. The method of claim 1, wherein the fusion protein is administered before, during, or after the subject develops PH.

9. The method of claim 1, wherein the fusion protein is part of a pharmaceutical composition.

10. The method of claim 9, wherein the pharmaceutical composition is formulated for modified release, sustained release, or controlled release, or a combination thereof.

11. The method of claim 9, wherein the pharmaceutical composition is formulated for oral, via inhalation, nasal, sublingual, buccal, subcutaneous, intradermal, intramuscular, intravenous, intraperitoneal, or parenteral administration.

* * * * *

SEQUENCE LISTING

```
<160> NUMBER OF SEQ ID NOS: 79

<210> SEQ ID NO 1
<211> LENGTH: 364
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 1
```

Thr Ile Pro Pro His Val Gln Lys Ser Val Asn Asn Asp Met Ile Val
1               5                   10                  15

Thr Asp Asn Asn Gly Ala Val Lys Phe Pro Gln Leu Cys Lys Phe Cys
            20                  25                  30

Asp Val Arg Phe Ser Thr Cys Asp Asn Gln Lys Ser Cys Met Ser Asn
        35                  40                  45

Cys Ser Ile Thr Ser Ile Cys Glu Lys Pro Gln Glu Val Cys Val Ala
    50                  55                  60

Val Trp Arg Lys Asn Asp Glu Asn Ile Thr Leu Glu Thr Val Cys His
65              70                  75                  80

Asp Pro Lys Leu Pro Tyr His Asp Phe Ile Leu Glu Asp Ala Ala Ser
                85                  90                  95

Pro Lys Cys Ile Met Lys Glu Lys Lys Pro Gly Glu Thr Phe Phe
            100                 105                 110

Met Cys Ser Cys Ser Ser Asp Glu Cys Asn Asp Asn Ile Ile Phe Ser
            115                 120                 125

Glu Glu Tyr Asn Thr Ser Asn Pro Asp Thr Gly Gly Val Glu Cys
    130                 135                 140

Pro Pro Cys Pro Ala Pro Pro Val Ala Gly Pro Ser Val Phe Leu Phe
145                 150                 155                 160

Pro Pro Lys Pro Lys Asp Thr Leu Met Ile Ser Arg Thr Pro Glu Val
                165                 170                 175

Thr Cys Val Val Val Asp Val Ser His Glu Asp Pro Glu Val Gln Phe
            180                 185                 190

Asn Trp Tyr Val Asp Gly Val Glu Val His Asn Ala Lys Thr Lys Pro
        195                 200                 205

Arg Glu Glu Gln Phe Asn Ser Thr Phe Arg Val Val Ser Val Leu Thr
    210                 215                 220

Val Val His Gln Asp Trp Leu Asn Gly Lys Glu Tyr Lys Cys Lys Val
225                 230                 235                 240

Ser Asn Lys Gly Leu Pro Ala Pro Ile Glu Lys Thr Ile Ser Lys Thr
                245                 250                 255

Lys Gly Gln Pro Arg Glu Pro Gln Val Tyr Thr Leu Pro Pro Ser Arg
            260                 265                 270

Glu Glu Met Thr Lys Asn Gln Val Ser Leu Thr Cys Leu Val Lys Gly
        275                 280                 285

Phe Tyr Pro Ser Asp Ile Ala Val Glu Trp Glu Ser Asn Gly Gln Pro
    290                 295                 300

Glu Asn Asn Tyr Lys Thr Thr Pro Pro Met Leu Asp Ser Asp Gly Ser
305                 310                 315                 320

Phe Phe Leu Tyr Ser Lys Leu Thr Val Asp Lys Ser Arg Trp Gln Gln
                325                 330                 335

Gly Asn Val Phe Ser Cys Ser Val Met His Glu Ala Leu His Asn His
            340                 345                 350

Tyr Thr Gln Lys Ser Leu Ser Leu Ser Pro Gly Lys
        355                 360

<210> SEQ ID NO 2
<211> LENGTH: 1164
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 2

```
atggatgcaa tgaagagagg gctctgctgt gtgctgctgc tgtgtggagc agtcttcgtt      60
tcgcccggcg ccacgatccc accgcacgtt cagaagtcgg ttaataacga catgatagtc     120
actgacaaca acggtgcagt caagtttcca caactgtgta aattttgtga tgtgagattt     180
tccacctgtg acaaccagaa atcctgcatg agcaactgca gcatcacctc catctgtgag     240
aagccacagg aagtctgtgt ggctgtatgg agaaagaatg acgagaacat aacactagag     300
acagtttgcc atgaccccaa gctcccctac catgacttta ttctggaaga tgctgcttct     360
ccaaagtgca ttatgaagga aaaaaaaaag cctggtgaga cttttcttca tgtgttcctgt     420
agctctgatg agtgcaatga acacatcatc ttctcagaag aatataacac cagcaatcct     480
gacaccggtg gtggagtcga gtgcccaccg tgcccagcac cacctgtggc aggaccgtca     540
gtcttcctct ccccccaaa acccaaggac accctcatga tctcccggac ccctgaggtc     600
acgtgcgtgg tggtggacgt gagccacgaa gaccccgagg tccagttcaa ctggtacgtg     660
gacggcgtgg aggtgcataa tgccaagaca aagccacggg aggagcagtt caacagcacg     720
ttccgtgtgg tcagcgtcct caccgtcgtg caccaggact ggctgaacgg caaggagtac     780
aagtgcaagg tctccaacaa aggcctccca gcccccatcg agaaaaccat ctccaaaacc     840
aaagggcagc cccgagaacc acaggtgtac accctgcccc catcccggga ggagatgacc     900
aagaaccagg tcagcctgac ctgcctggtc aaaggcttct accccagcga catcgccgtg     960
gagtgggaga gcaatgggca gccggagaac aactacaaga ccacacctcc catgctggac    1020
tccgacggct ccttcttcct ctacagcaag ctcaccgtgg acaagagcag gtggcagcag    1080
gggaacgtct tctcatgctc cgtgatgcat gaggctctgc acaaccacta cacgcagaag    1140
agcctctccc tgtctccggg taaa                                            1164
```

<210> SEQ ID NO 3
<211> LENGTH: 101
<212> TYPE: PRT
<213> ORGANISM: Homo sapiens

<400> SEQUENCE: 3

```
Gln Leu Cys Lys Phe Cys Asp Val Arg Phe Ser Thr Cys Asp Asn Gln
1               5                   10                  15
Lys Ser Cys Met Ser Asn Cys Ser Ile Thr Ser Ile Cys Glu Lys Pro
            20                  25                  30
Gln Glu Val Cys Val Ala Val Trp Arg Lys Asn Asp Glu Asn Ile Thr
        35                  40                  45
Leu Glu Thr Val Cys His Asp Pro Lys Leu Pro Tyr His Asp Phe Ile
    50                  55                  60
Leu Glu Asp Ala Ala Ser Pro Lys Cys Ile Met Lys Glu Lys Lys Lys
65                  70                  75                  80
Pro Gly Glu Thr Phe Phe Met Cys Ser Cys Ser Ser Asp Glu Cys Asn
                85                  90                  95
Asp Asn Ile Ile Phe
            100
```

<210> SEQ ID NO 4
<211> LENGTH: 101
<212> TYPE: PRT
<213> ORGANISM: Homo sapiens

<400> SEQUENCE: 4

```
Gln Leu Cys Lys Phe Cys Asp Val Arg Phe Ser Thr Cys Asp Asn Gln
1               5                   10                  15

Lys Ser Cys Met Ser Asn Cys Ser Ile Thr Ser Ile Cys Glu Lys Pro
            20                  25                  30

Gln Glu Val Cys Val Ala Val Trp Arg Lys Asn Asp Glu Asn Ile Thr
        35                  40                  45

Leu Glu Thr Val Cys His Asp Pro Lys Leu Pro Tyr His Asp Phe Ile
    50                  55                  60

Leu Glu Asp Ala Ala Ser Pro Lys Cys Ile Met Lys Glu Lys Lys
65                  70                  75                  80

Pro Gly Glu Thr Phe Phe Met Cys Ser Cys Ser Ser Asp Glu Cys Asn
                85                  90                  95

Asp Asn Ile Ile Phe
            100
```

<210> SEQ ID NO 5
<211> LENGTH: 79
<212> TYPE: PRT
<213> ORGANISM: Homo sapiens

<400> SEQUENCE: 5

```
Ala Leu Gln Cys Phe Cys His Leu Cys Thr Lys Asp Asn Phe Thr Cys
1               5                   10                  15

Val Thr Asp Gly Leu Cys Phe Val Ser Val Thr Glu Thr Thr Asp Lys
            20                  25                  30

Val Ile His Asn Ser Met Cys Ile Ala Glu Ile Asp Leu Ile Pro Arg
        35                  40                  45

Asp Arg Pro Phe Val Cys Ala Pro Ser Ser Lys Thr Gly Ser Val Thr
    50                  55                  60

Thr Thr Tyr Cys Cys Asn Gln Asp His Cys Asn Lys Ile Glu Leu
65                  70                  75
```

<210> SEQ ID NO 6
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

```
Pro Phe Lys Val Ala Gly Asn Asn Asp Thr Val Ile Met Asp Asn Asn
1               5                   10                  15

Val Ser Lys Gln Val His Pro Pro Ile
            20                  25
```

<210> SEQ ID NO 7
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 7

```
Asp Pro Asn Ser Thr Asn Tyr Glu Glu Ser
1               5                   10
```

<210> SEQ ID NO 8
<211> LENGTH: 50
<212> TYPE: PRT

```
<213> ORGANISM: Artificial Sequence
<220> FEATURE:
<223> OTHER INFORMATION: Description of Artificial Sequence: Synthetic
      polypeptide

<400> SEQUENCE: 8

Pro Phe Lys Val Ala Gly Asn Asn Asp Thr Val Ile Met Asp Asn Asn
1               5                   10                  15

Ile His Arg Leu Pro His Ala Thr Arg Asn Cys Ser Pro Cys Ile Ile
            20                  25                  30

Glu Asp Lys Gln Ala Glu Met Glu Val Asp Ser Lys Gln Val His Pro
        35                  40                  45

Pro Ile
    50

<210> SEQ ID NO 9
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 9

Thr Ala Gly Pro Leu Leu Ala Ala
1               5

<210> SEQ ID NO 10
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 10

Glu Val Pro Gly Leu Gly Pro Ser Ser Lys Val Thr Thr Pro
1               5                   10

<210> SEQ ID NO 11
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 11

Glu Ser Arg Gly Leu Ile Ala
1               5

<210> SEQ ID NO 12
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 12

Ile Asn Tyr Tyr Pro Pro Lys Pro Thr Val Pro Asn Ser Thr Pro Gln
1               5                   10                  15

Thr Val Glu Met Glu
            20
```

```
<210> SEQ ID NO 13
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 13

Thr Glu Ala Glu Gly Arg Gly Ser
1               5

<210> SEQ ID NO 14
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 14

Thr Pro Ala Thr Pro Pro Glu Tyr Thr Val Glu Pro Gly Gly Ala
1               5                   10                  15

Glu

<210> SEQ ID NO 15
<211> LENGTH: 31
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 15

Asp Glu Pro Ala Leu Thr Val Gly Asn Glu Ser Lys Lys Gln Asp Ser
1               5                   10                  15

Asp Ser Lys Met Gly Thr Gly His Leu Met Ser Asp Leu Asn Gln
                20                  25                  30

<210> SEQ ID NO 16
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 16

Arg Ile Ser Gly Asp Phe Phe Pro Gly Ile Val Val Pro
1               5                   10

<210> SEQ ID NO 17
<211> LENGTH: 101
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 17

Phe Ile Ile Asn Asp Asn Cys Glu Asp Ser Ser Cys Ser Cys Met Phe
1               5                   10                  15

Phe Thr Glu Gly Pro Lys Lys Lys Glu Lys Met Ile Cys Lys Pro Ser
                20                  25                  30

Ala Ala Asp Glu Leu Ile Phe Asp His Tyr Pro Leu Lys Pro Asp His
                35                  40                  45
```

```
Cys Val Thr Glu Leu Thr Ile Asn Glu Asp Asn Lys Arg Trp Val Ala
    50                  55                  60
Val Cys Val Glu Gln Pro Lys Glu Cys Ile Ser Thr Ile Ser Cys Asn
65                  70                  75                  80
Ser Met Cys Ser Lys Gln Asn Asp Cys Thr Ser Phe Arg Val Asp Cys
                85                  90                  95
Phe Lys Cys Leu Gln
            100
```

```
<210> SEQ ID NO 18
<211> LENGTH: 101
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 18

Phe Ile Ile Asn Asp Asn Cys Glu Asp Ser Ser Cys Ser Cys Met Phe
1               5                   10                  15
Phe Thr Glu Gly Pro Lys Lys Lys Glu Lys Met Ile Cys Lys Pro Ser
                20                  25                  30
Ala Ala Asp Glu Leu Ile Phe Asp His Tyr Pro Leu Lys Pro Asp His
            35                  40                  45
Cys Val Thr Glu Leu Thr Ile Asn Glu Asp Asn Lys Arg Trp Val Ala
    50                  55                  60
Val Cys Val Glu Gln Pro Lys Glu Cys Ile Ser Thr Ile Ser Cys Asn
65                  70                  75                  80
Ser Met Cys Ser Lys Gln Asn Asp Cys Thr Ser Phe Arg Val Asp Cys
                85                  90                  95
Phe Lys Cys Leu Gln
            100
```

```
<210> SEQ ID NO 19
<211> LENGTH: 79
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 19

Leu Glu Ile Lys Asn Cys His Asp Gln Asn Cys Cys Tyr Thr Thr Thr
1               5                   10                  15
Val Ser Gly Thr Lys Ser Ser Pro Ala Cys Val Phe Pro Arg Asp Arg
                20                  25                  30
Pro Ile Leu Asp Ile Glu Ala Ile Cys Met Ser Asn His Ile Val Lys
            35                  40                  45
Asp Thr Thr Glu Thr Val Ser Val Phe Cys Leu Gly Asp Thr Val Cys
    50                  55                  60
Thr Phe Asn Asp Lys Thr Cys Leu His Cys Phe Cys Gln Leu Ala
65                  70                  75
```

```
<210> SEQ ID NO 20
<211> LENGTH: 92
<212> TYPE: PRT
<213> ORGANISM: Artificial Sequence
<220> FEATURE:
<223> OTHER INFORMATION: Description of Artificial Sequence: Synthetic
      polypeptide
```

<400> SEQUENCE: 20

Pro Phe Tyr Ser Phe Lys Glu Asn Cys Met Asn Gly Glu Cys Cys
1               5                   10                  15

Phe Tyr Val Glu Pro Ser Asp Lys Lys Glu Val Cys Asp Thr Arg Asp
            20                  25                  30

Tyr Cys Asn Ile Asp Asp Leu Trp Cys Gly Gln Lys Val Ile Glu Ile
        35                  40                  45

Ser Gly Ser Ile Asn Lys Trp Thr Ala Phe Cys His Arg Arg Lys Asp
50                  55                  60

Lys Asp Gly Tyr Cys Pro Glu Val Gly Thr Gln Asn Thr Arg Asp Lys
65                  70                  75                  80

Glu Trp Asn Ala Asn Phe Phe Leu Cys Glu Gln Thr
                85                  90

<210> SEQ ID NO 21
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 21

Thr Pro Ala Thr Pro Pro Glu Tyr Thr Val Glu Pro Gly Gly Ala
1               5                   10                  15

Glu Pro Leu His Thr Phe Arg Glu Asn Cys Phe Asn Gly Glu Cys Cys
            20                  25                  30

Cys Phe Tyr Val Gln Pro Asn Glu Glu Thr Ala Val Cys Glu Gln Arg
        35                  40                  45

Asp Tyr Cys Asn Phe Asp Asp Leu Trp Cys Gly Lys Lys Val Leu Glu
50                  55                  60

Ile Thr Gly Ser Ser Asn Arg Trp Ser Ala Tyr Cys His Leu Arg Lys
65                  70                  75                  80

Asp Gln Glu Gly Glu Cys Arg Glu Leu Gly Ser Gln Asn Thr Arg Glu
                85                  90                  95

Leu Glu Trp Asn Ala Asn Tyr Tyr Ile Cys Glu Arg
                100                 105

<210> SEQ ID NO 22
<211> LENGTH: 98
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 22

Arg Ile Ser Gly Asp Phe Phe Pro Gly Ile Val Val Pro Pro Leu Thr
1               5                   10                  15

Pro Gln Leu Tyr Gln Asn Cys Leu Asn Thr Arg Cys Cys Glu Ile Thr
            20                  25                  30

Arg Arg Leu Gln Ala Lys Pro Ser Asp Lys Cys Gln Phe Asp Ser Gly
        35                  40                  45

Glu Tyr Lys Met Cys Gly Ser Ala Leu Thr Thr Glu Gly Gln Asp Asp
50                  55                  60

Glu Glu Ile Ile Ala Phe Cys His Gly Asn Thr Ile Cys Thr Asn Asn
65                  70                  75                  80

```
Ile Ala Asp Asp Pro Cys His Gly Ser Cys Tyr Cys Lys Leu Phe Pro
                85                  90                  95

Leu Thr

<210> SEQ ID NO 23
<211> LENGTH: 35
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 23

Pro Phe Lys Val Ala Gly Asn Asn Asp Thr Val Ile Met Asp Asn Asn
1               5                   10                  15

Val Ser Lys Gln Val His Pro Pro Ile Asp Pro Asn Ser Thr Asn Tyr
            20                  25                  30

Glu Glu Ser
        35

<210> SEQ ID NO 24
<211> LENGTH: 60
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 24

Pro Phe Lys Val Ala Gly Asn Asn Asp Thr Val Ile Met Asp Asn Asn
1               5                   10                  15

Ile His Arg Leu Pro His Ala Thr Arg Asn Cys Ser Pro Cys Ile Ile
            20                  25                  30

Glu Asp Lys Gln Ala Glu Met Glu Val Asp Ser Lys Gln Val His Pro
        35                  40                  45

Pro Ile Asp Pro Asn Ser Thr Asn Tyr Glu Glu Ser
    50                  55                  60

<210> SEQ ID NO 25
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 25

Thr Glu Ala Glu Gly Arg Gly Ser Thr Pro Ala Thr Pro Pro Pro Glu
1               5                   10                  15

Tyr Thr Val Glu Pro Gly Gly Ala Glu
            20                  25

<210> SEQ ID NO 26
<211> LENGTH: 44
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 26

Asp Glu Pro Ala Leu Thr Val Gly Asn Glu Ser Lys Lys Gln Asp Ser
1               5                   10                  15
```

```
Asp Ser Lys Met Gly Thr Gly His Leu Met Ser Asp Leu Asn Gln Arg
            20                  25                  30

Ile Ser Gly Asp Phe Phe Pro Gly Ile Val Val Pro
        35                  40
```

<210> SEQ ID NO 27
<211> LENGTH: 44
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 27

```
Asp Glu Pro Ala Leu Thr Val Gly Asn Glu Ser Lys Lys Gln Asp Ser
1               5                   10                  15

Asp Ser Lys Met Gly Thr Gly His Leu Met Ser Asp Leu Asn Gly Arg
            20                  25                  30

Ile Ser Gly Asp Phe Phe Pro Gly Ile Val Val Pro
        35                  40
```

<210> SEQ ID NO 28
<211> LENGTH: 35
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 28

```
Pro Phe Lys Val Ala Gly Asn Asn Asp Thr Val Ile Met Asp Asn Asn
1               5                   10                  15

Val Ser Lys Gln Val His Pro Pro Gly Asp Pro Asn Ser Thr Asn Tyr
            20                  25                  30

Glu Glu Ser
        35
```

<210> SEQ ID NO 29
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 29

```
Thr Glu Ala Glu Gly Arg Gly Ser Thr Pro Thr Pro Pro Pro Glu
1               5                   10                  15

Gly Thr Val Glu Pro Gly Gly Ala Glu
            20                  25
```

<210> SEQ ID NO 30
<211> LENGTH: 60
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 30

```
Pro Phe Lys Val Ala Gly Asn Asn Asp Thr Val Ile Met Asp Asn Asn
1               5                   10                  15

Ile His Arg Leu Pro His Ala Thr Arg Asn Cys Ser Pro Cys Ile Ile
            20                  25                  30
```

Glu Asp Lys Gln Ala Glu Met Glu Val Asp Ser Lys Gln Val His Arg
            35                  40                  45

Gly Gly Asp Pro Asn Ser Thr Asn Tyr Glu Glu Ser
        50                  55                  60

<210> SEQ ID NO 31
<211> LENGTH: 35
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 31

Pro Phe Lys Val Ala Gly Asn Asn Asp Thr Val Ile Met Asp Asn Asn
1               5                   10                  15

Val Ser Lys Gln Val His Pro Gly Gly Asp Pro Asn Ser Thr Asn Tyr
            20                  25                  30

Glu Glu Ser
        35

<210> SEQ ID NO 32
<211> LENGTH: 35
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 32

Pro Phe Lys Val Ala Gly Asn Asn Asp Thr Val Ile Met Asp Asn Asn
1               5                   10                  15

Val Ser Lys Gln Val His Arg Gly Gly Asp Pro Asn Ser Thr Asn Tyr
            20                  25                  30

Glu Glu Ser
        35

<210> SEQ ID NO 33
<211> LENGTH: 60
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 33

Pro Phe Lys Val Ala Gly Asn Asn Asp Thr Val Ile Met Asp Asn Asn
1               5                   10                  15

Ile His Arg Leu Pro His Ala Thr Arg Asn Cys Ser Pro Cys Ile Ile
            20                  25                  30

Glu Asp Lys Gln Ala Glu Met Gly Gly Ser Gly Gly Gly Ser Gly
            35                  40                  45

Gly Gly Ser Pro Asn Ser Thr Asn Tyr Glu Glu Ser
        50                  55                  60

<210> SEQ ID NO 34
<211> LENGTH: 35
<212> TYPE: PRT
<213> ORGANISM: Artificial Sequence
<220> FEATURE:
<223> OTHER INFORMATION: Description of Artificial Sequence: Synthetic
      polypeptide -continued

```
<400> SEQUENCE: 34

Pro Phe Lys Val Ala Gly Asn Asn Asp Thr Val Ile Met Asp Asn Asn
1               5                   10                  15

Val Ser Lys Gly Gly Ser Gly Gly Gly Ser Pro Asn Ser Thr Asn Tyr
            20                  25                  30

Glu Glu Ser
        35

<210> SEQ ID NO 35
<211> LENGTH: 35
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 35

Pro Phe Lys Val Ala Gly Asn Asn Asp Thr Val Ile Met Asp Gly Gly
1               5                   10                  15

Gly Ser Gly Gly Gly Ser Gly Gly Gly Ser Pro Asn Ser Thr Asn Tyr
            20                  25                  30

Glu Glu Ser
        35

<210> SEQ ID NO 36
<211> LENGTH: 60
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 36

Pro Phe Lys Val Ala Gly Asn Asn Asp Thr Val Ile Met Asp Asn Asn
1               5                   10                  15

Gly Gly Ser Gly Gly Gly Ser Gly Gly Gly Ser Gly Gly Gly Ser Gly
            20                  25                  30

Gly Gly Ser Gly Gly Gly Ser Gly Gly Gly Ser Lys Gln Val His Pro
        35                  40                  45

Pro Ile Asp Pro Asn Ser Thr Asn Tyr Glu Glu Ser
    50                  55                  60

<210> SEQ ID NO 37
<211> LENGTH: 60
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 37

Pro Phe Lys Val Ala Gly Asn Asn Asp Thr Val Ile Met Asp Asn Asn
1               5                   10                  15

Gly Gly Ser Gly Gly Gly Ser Gly Gly Gly Ser Gly Gly Gly Ser Gly
            20                  25                  30

Gly Gly Ser Gly Gly Gly Ser Gly Gly Gly Ser Gly Gly Gly Ser Gly
        35                  40                  45

Gly Gly Asp Pro Asn Ser Thr Asn Tyr Glu Glu Ser
    50                  55                  60

<210> SEQ ID NO 38
```

<211> LENGTH: 35
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 38

Pro Phe Lys Val Ala Gly Asn Asn Asp Thr Val Ile Met Asp Asn Asn
1               5                   10                  15

Val Ser Lys Gln Val His Pro Pro Ile Asp Pro Asn Ser Thr Asn Tyr
            20                  25                  30

Glu Glu Ser
        35

<210> SEQ ID NO 39
<211> LENGTH: 48
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 39

Pro Phe Lys Val Ala Gly Asn Asn Asp Ile Val Ile Met Asp Asn Asn
1               5                   10                  15

Val Ser Lys Gln Val His Pro Pro Ile Met Asp Asn Asn Val Ser Lys
            20                  25                  30

Gln Val His Pro Pro Ile Asp Pro Asn Ser Thr Asn Tyr Glu Glu Ser
        35                  40                  45

<210> SEQ ID NO 40
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 40

Pro Phe Lys Val Ala Gly Asn Asn Asp Thr Val Ile Met Asp Asn Asn
1               5                   10                  15

Val Ser Lys Gln Val His Pro Pro Asn Ser Thr Asn Tyr Glu Glu Ser
            20                  25                  30

<210> SEQ ID NO 41
<211> LENGTH: 43
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 41

Pro Phe Lys Val Ala Gly Asn Asn Asp Ile Val Ile Met Asp Asn Asn
1               5                   10                  15

Val Ser Lys Gln Val His Pro Pro Ile Gly Gly Gly Gly Gly Gly
            20                  25                  30

Gly Asp Pro Asn Ser Thr Asn Tyr Glu Glu Ser
        35                  40

<210> SEQ ID NO 42
<211> LENGTH: 47
<212> TYPE: PRT

```
<213> ORGANISM: Artificial Sequence
<220> FEATURE:
<223> OTHER INFORMATION: Description of Artificial Sequence: Synthetic
      polypeptide

<400> SEQUENCE: 42

Pro Phe Lys Val Ala Gly Asn Asn Asp Thr Val Ile Met Asp Asn Asn
1               5                   10                  15

Val Ser Lys Gln Val His Pro Pro Ile Ser Gly Gly Ser Gly Gly
            20                  25                  30

Gly Ser Gly Gly Gly Asp Pro Asn Ser Thr Asn Tyr Glu Glu Ser
        35                  40                  45

<210> SEQ ID NO 43
<211> LENGTH: 60
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 43

Pro Phe Lys Val Ala Gly Asn Asn Asp Thr Val Ile Met Asp Asn Asn
1               5                   10                  15

Ile His Arg Leu Pro His Ala Thr Arg Asn Cys Ser Pro Cys Ile Ile
            20                  25                  30

Glu Asp Lys Gln Ala Glu Met Glu Val Asp Ser Lys Gln Val His Pro
        35                  40                  45

Pro Ile Asp Pro Asn Ser Thr Asn Tyr Glu Glu Ser
    50                  55                  60

<210> SEQ ID NO 44
<211> LENGTH: 53
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 44

Pro Phe Lys Val Ala Gly Asn Asn Asp Thr Val Ile Met Asp Asn Asn
1               5                   10                  15

Ile His Arg Leu Pro His Ala Thr Arg Glu Asp Lys Gln Ala Glu Met
            20                  25                  30

Glu Val Asp Ser Lys Gln Val His Pro Pro Ile Asp Pro Asn Ser Thr
        35                  40                  45

Asn Tyr Glu Glu Ser
    50

<210> SEQ ID NO 45
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 45

Thr Glu Ala Glu Gly Arg Gly Ser Thr Pro Ala Thr Pro Pro Pro Glu
1               5                   10                  15

Tyr Thr Val Glu Pro Gly Gly Ala Glu
            20                  25
```

<210> SEQ ID NO 46
<211> LENGTH: 35
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 46

Thr Glu Ala Glu Gly Arg Gly Ser Gly Gly Gly Gly Gly Gly Gly
1               5                   10                  15

Gly Gly Thr Pro Ala Thr Pro Pro Glu Tyr Thr Val Glu Pro Gly
                20                  25                  30

Gly Ala Glu
        35

<210> SEQ ID NO 47
<211> LENGTH: 44
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 47

Asp Glu Pro Ala Leu Thr Val Gly Asn Glu Ser Lys Lys Gln Asp Ser
1               5                   10                  15

Asp Ser Lys Met Gly Thr Gly His Leu Met Ser Asp Leu Asn Gln Arg
                20                  25                  30

Ile Ser Gly Asp Phe Phe Pro Gly Ile Val Val Pro
        35                  40

<210> SEQ ID NO 48
<211> LENGTH: 40
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 48

Asp Glu Pro Ala Leu Thr Val Gly Asn Glu Ser Lys Lys Gln Asp Ser
1               5                   10                  15

Asp Ser Lys Met Gly Thr Gly His Ser Asp Leu Asn Gln Arg Ile Ser
                20                  25                  30

Gly Asp Pro Gly Ile Val Val Pro
        35                  40

<210> SEQ ID NO 49
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 49
tgagtggctg tcttttgacg                                            20

<210> SEQ ID NO 50
<211> LENGTH: 20
<212> TYPE: DNA
<213> ORGANISM: Artificial Sequence
<220> FEATURE:

```
<223> OTHER INFORMATION: Description of Artificial Sequence: Synthetic
      primer

<400> SEQUENCE: 50
ttctctgtgg agctgaagca                                                  20

<210> SEQ ID NO 51
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 51
cacgcctctc ttgtttcctc                                                  20

<210> SEQ ID NO 52
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 52
ttttccaagg gcaatgaaag                                                  20

<210> SEQ ID NO 53
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 53
gaaggctgca ctcaggaaac                                                  20

<210> SEQ ID NO 54
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 54
gctgcttggc tatgtgttca                                                  20

<210> SEQ ID NO 55
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 55
ctttatcctg ggtctccctg                                                  20

<210> SEQ ID NO 56
<211> LENGTH: 20
<212> TYPE: DNA
<213> ORGANISM: Artificial Sequence
<220> FEATURE:
<223> OTHER INFORMATION: Description of Artificial Sequence: Synthetic
``` primer

<400> SEQUENCE: 56
tgatgcctcc ctgacataca                                               20

<210> SEQ ID NO 57
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 57
aataatctgg gtaaggcc                                                 18

<210> SEQ ID NO 58
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 58
gcagaacgaa cgcaacctat ca                                            22

<210> SEQ ID NO 59
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 59
tggacgaaca gcaggtgaac g                                             21

<210> SEQ ID NO 60
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 60
gcactgatct cgccgttcag g                                             21

<210> SEQ ID NO 61
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 61
tgtcaccaac tgggacgata                                               20

<210> SEQ ID NO 62
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 62
accctcatag atgggcacag                                         20

<210> SEQ ID NO 63
<211> LENGTH: 137
<212> TYPE: PRT
<213> ORGANISM: Homo sapiens

<400> SEQUENCE: 63

Thr Ile Pro Pro His Val Gln Lys Ser Val Asn Asp Met Ile Val
1               5                   10                  15

Thr Asp Asn Asn Gly Ala Val Lys Phe Pro Gln Leu Cys Lys Phe Cys
            20                  25                  30

Asp Val Arg Phe Ser Thr Cys Asp Asn Gln Lys Ser Cys Met Ser Asn
        35                  40                  45

Cys Ser Ile Thr Ser Ile Cys Glu Lys Pro Gln Glu Val Cys Val Ala
    50                  55                  60

Val Trp Arg Lys Asn Asp Glu Asn Ile Thr Leu Glu Thr Val Cys His
65                  70                  75                  80

Asp Pro Lys Leu Pro Tyr His Asp Phe Ile Leu Glu Asp Ala Ala Ser
                85                  90                  95

Pro Lys Cys Ile Met Lys Glu Lys Lys Pro Gly Glu Thr Phe Phe
            100                 105                 110

Met Cys Ser Cys Ser Ser Asp Glu Cys Asn Asp Asn Ile Ile Phe Ser
        115                 120                 125

Glu Glu Tyr Asn Thr Ser Asn Pro Asp
    130                 135

<210> SEQ ID NO 64
<211> LENGTH: 222
<212> TYPE: PRT
<213> ORGANISM: Homo sapiens

<400> SEQUENCE: 64

Glu Cys Pro Pro Cys Pro Ala Pro Pro Val Ala Gly Pro Ser Val Phe
1               5                   10                  15

Leu Phe Pro Pro Lys Pro Lys Asp Thr Leu Met Ile Ser Arg Thr Pro
            20                  25                  30

Glu Val Thr Cys Val Val Val Asp Val Ser His Glu Asp Pro Glu Val
        35                  40                  45

Gln Phe Asn Trp Tyr Val Asp Gly Val Glu Val His Asn Ala Lys Thr
    50                  55                  60

Lys Pro Arg Glu Glu Gln Phe Asn Ser Thr Phe Arg Val Val Ser Val
65                  70                  75                  80

Leu Thr Val Val His Gln Asp Trp Leu Asn Gly Lys Glu Tyr Lys Cys
                85                  90                  95

Lys Val Ser Asn Lys Gly Leu Pro Ala Pro Ile Glu Lys Thr Ile Ser
            100                 105                 110

Lys Thr Lys Gly Gln Pro Arg Glu Pro Gln Val Tyr Thr Leu Pro Pro
        115                 120                 125

Ser Arg Glu Glu Met Thr Lys Asn Gln Val Ser Leu Thr Cys Leu Val
    130                 135                 140

Lys Gly Phe Tyr Pro Ser Asp Ile Ala Val Glu Trp Glu Ser Asn Gly
145                 150                 155                 160

Gln Pro Glu Asn Asn Tyr Lys Thr Thr Pro Pro Met Leu Asp Ser Asp

```
            165                 170                 175
Gly Ser Phe Phe Leu Tyr Ser Lys Leu Thr Val Asp Lys Ser Arg Trp
        180                 185                 190

Gln Gln Gly Asn Val Phe Ser Cys Ser Val Met His Glu Ala Leu His
    195                 200                 205

Asn His Tyr Thr Gln Lys Ser Leu Ser Leu Ser Pro Gly Lys
    210                 215                 220

<210> SEQ ID NO 65
<211> LENGTH: 15
<212> TYPE: PRT
<213> ORGANISM: Homo sapiens

<400> SEQUENCE: 65

Glu Pro Lys Ser Cys Asp Lys Thr His Thr Cys Pro Pro Cys Pro
1               5                   10                  15

<210> SEQ ID NO 66
<211> LENGTH: 12
<212> TYPE: PRT
<213> ORGANISM: Homo sapiens

<400> SEQUENCE: 66

Glu Arg Lys Cys Cys Val Glu Cys Pro Pro Cys Pro
1               5                   10

<210> SEQ ID NO 67
<211> LENGTH: 62
<212> TYPE: PRT
<213> ORGANISM: Homo sapiens

<400> SEQUENCE: 67

Glu Leu Lys Thr Pro Leu Gly Asp Thr Thr His Thr Cys Pro Arg Cys
1               5                   10                  15

Pro Glu Pro Lys Ser Cys Asp Thr Pro Pro Cys Pro Arg Cys Pro
            20                  25                  30

Glu Pro Lys Ser Cys Asp Thr Pro Pro Cys Pro Arg Cys Pro Glu
        35                  40                  45

Pro Lys Ser Cys Asp Thr Pro Pro Cys Pro Arg Cys Pro
    50                  55                  60

<210> SEQ ID NO 68
<211> LENGTH: 12
<212> TYPE: PRT
<213> ORGANISM: Homo sapiens

<400> SEQUENCE: 68

Glu Ser Lys Tyr Gly Pro Pro Cys Pro Ser Cys Pro
1               5                   10

<210> SEQ ID NO 69
<211> LENGTH: 217
<212> TYPE: PRT
<213> ORGANISM: Homo sapiens

<400> SEQUENCE: 69

Ala Pro Glu Leu Leu Gly Gly Pro Ser Val Phe Leu Phe Pro Pro Lys
1               5                   10                  15

Pro Lys Asp Thr Leu Met Ile Ser Arg Thr Pro Glu Val Thr Cys Val
            20                  25                  30

Val Val Asp Val Ser His Glu Asp Pro Glu Val Lys Phe Asn Trp Tyr
```

```
              35                  40                  45
Val Asp Gly Val Glu Val His Asn Ala Lys Thr Lys Pro Arg Glu Glu
 50                  55                  60

Gln Tyr Asn Ser Thr Tyr Arg Val Val Ser Val Leu Thr Val Leu His
65                  70                  75                  80

Gln Asp Trp Leu Asn Gly Lys Glu Tyr Lys Cys Lys Val Ser Asn Lys
                 85                  90                  95

Ala Leu Pro Ala Pro Ile Glu Lys Thr Ile Ser Lys Ala Lys Gly Gln
            100                 105                 110

Pro Arg Glu Pro Gln Val Tyr Thr Leu Pro Pro Ser Arg Asp Glu Leu
        115                 120                 125

Thr Lys Asn Gln Val Ser Leu Thr Cys Leu Val Lys Gly Phe Tyr Pro
    130                 135                 140

Ser Asp Ile Ala Val Glu Trp Glu Ser Asn Gly Gln Pro Glu Asn Asn
145                 150                 155                 160

Tyr Lys Thr Thr Pro Pro Val Leu Asp Ser Asp Gly Ser Phe Phe Leu
                165                 170                 175

Tyr Ser Lys Leu Thr Val Asp Lys Ser Arg Trp Gln Gln Gly Asn Val
            180                 185                 190

Phe Ser Cys Ser Val Met His Glu Ala Leu His Asn His Tyr Thr Gln
        195                 200                 205

Lys Ser Leu Ser Leu Ser Pro Gly Lys
    210                 215

<210> SEQ ID NO 70
<211> LENGTH: 216
<212> TYPE: PRT
<213> ORGANISM: Homo sapiens

<400> SEQUENCE: 70

Ala Pro Pro Val Ala Gly Pro Ser Val Phe Leu Phe Pro Pro Lys Pro
1               5                   10                  15

Lys Asp Thr Leu Met Ile Ser Arg Thr Pro Glu Val Thr Cys Val Val
            20                  25                  30

Val Asp Val Ser His Glu Asp Pro Glu Val Gln Phe Asn Trp Tyr Val
        35                  40                  45

Asp Gly Val Glu Val His Asn Ala Lys Thr Lys Pro Arg Glu Glu Gln
    50                  55                  60

Phe Asn Ser Thr Phe Arg Val Val Ser Val Leu Thr Val Val His Gln
65                  70                  75                  80

Asp Trp Leu Asn Gly Lys Glu Tyr Lys Cys Lys Val Ser Asn Lys Gly
                85                  90                  95

Leu Pro Ala Pro Ile Glu Lys Thr Ile Ser Lys Thr Lys Gly Gln Pro
            100                 105                 110

Arg Glu Pro Gln Val Tyr Thr Leu Pro Pro Ser Arg Glu Glu Met Thr
        115                 120                 125

Lys Asn Gln Val Ser Leu Thr Cys Leu Val Lys Gly Phe Tyr Pro Ser
    130                 135                 140

Asp Ile Ala Val Glu Trp Glu Ser Asn Gly Gln Pro Glu Asn Asn Tyr
145                 150                 155                 160

Lys Thr Thr Pro Pro Met Leu Asp Ser Asp Gly Ser Phe Phe Leu Tyr
                165                 170                 175

Ser Lys Leu Thr Val Asp Lys Ser Arg Trp Gln Gln Gly Asn Val Phe
            180                 185                 190
```

Ser Cys Ser Val Met His Glu Ala Leu His Asn His Tyr Thr Gln Lys
        195                 200                 205

Ser Leu Ser Leu Ser Pro Gly Lys
    210                 215

<210> SEQ ID NO 71
<211> LENGTH: 217
<212> TYPE: PRT
<213> ORGANISM: Homo sapiens

<400> SEQUENCE: 71

Ala Pro Glu Leu Leu Gly Gly Pro Ser Val Phe Leu Phe Pro Pro Lys
1               5                   10                  15

Pro Lys Asp Thr Leu Met Ile Ser Arg Thr Pro Glu Val Thr Cys Val
            20                  25                  30

Val Val Asp Val Ser His Glu Asp Pro Glu Val Gln Phe Lys Trp Tyr
        35                  40                  45

Val Asp Gly Val Gln Val His Asn Ala Lys Thr Lys Pro Arg Glu Gln
    50                  55                  60

Gln Phe Asn Ser Thr Phe Arg Val Val Ser Val Leu Thr Val Leu His
65                  70                  75                  80

Gln Asn Trp Leu Asp Gly Lys Glu Tyr Lys Cys Lys Val Ser Asn Lys
                85                  90                  95

Ala Leu Pro Ala Pro Ile Glu Lys Thr Ile Ser Lys Thr Lys Gly Gln
            100                 105                 110

Pro Arg Glu Pro Gln Val Tyr Thr Leu Pro Pro Ser Arg Glu Glu Met
        115                 120                 125

Thr Lys Asn Gln Val Ser Leu Thr Cys Leu Val Lys Gly Phe Tyr Pro
    130                 135                 140

Ser Asp Ile Ala Val Glu Trp Glu Ser Ser Gly Gln Pro Glu Asn Asn
145                 150                 155                 160

Tyr Asn Thr Thr Pro Pro Met Leu Asp Ser Asp Gly Ser Phe Phe Leu
                165                 170                 175

Tyr Ser Lys Leu Thr Val Asp Lys Ser Arg Trp Gln Gln Gly Asn Ile
            180                 185                 190

Phe Ser Cys Ser Val Met His Glu Ala Leu His Asn Arg Phe Thr Gln
        195                 200                 205

Lys Ser Leu Ser Leu Ser Pro Gly Lys
    210                 215

<210> SEQ ID NO 72
<211> LENGTH: 217
<212> TYPE: PRT
<213> ORGANISM: Homo sapiens

<400> SEQUENCE: 72

Ala Pro Glu Phe Leu Gly Gly Pro Ser Val Phe Leu Phe Pro Pro Lys
1               5                   10                  15

Pro Lys Asp Thr Leu Met Ile Ser Arg Thr Pro Glu Val Thr Cys Val
            20                  25                  30

Val Val Asp Val Ser Gln Glu Asp Pro Glu Val Gln Phe Asn Trp Tyr
        35                  40                  45

Val Asp Gly Val Glu Val His Asn Ala Lys Thr Lys Pro Arg Glu Glu
    50                  55                  60

Gln Phe Asn Ser Thr Tyr Arg Val Val Ser Val Leu Thr Val Leu His
65                  70                  75                  80

Gln Asp Trp Leu Asn Gly Lys Glu Tyr Lys Cys Lys Val Ser Asn Lys
                 85                  90                  95

Gly Leu Pro Ser Ser Ile Glu Lys Thr Ile Ser Lys Ala Lys Gly Gln
            100                 105                 110

Pro Arg Glu Pro Gln Val Tyr Thr Leu Pro Pro Ser Gln Glu Glu Met
        115                 120                 125

Thr Lys Asn Gln Val Ser Leu Thr Cys Leu Val Lys Gly Phe Tyr Pro
    130                 135                 140

Ser Asp Ile Ala Val Glu Trp Glu Ser Asn Gly Gln Pro Glu Asn Asn
145                 150                 155                 160

Tyr Lys Thr Thr Pro Pro Val Leu Asp Ser Asp Gly Ser Phe Phe Leu
                165                 170                 175

Tyr Ser Arg Leu Thr Val Asp Lys Ser Arg Trp Gln Glu Gly Asn Val
            180                 185                 190

Phe Ser Cys Ser Val Met His Glu Ala Leu His Asn His Tyr Thr Gln
        195                 200                 205

Lys Ser Leu Ser Leu Ser Leu Gly Lys
    210                 215

<210> SEQ ID NO 73
<211> LENGTH: 107
<212> TYPE: PRT
<213> ORGANISM: Homo sapiens

<400> SEQUENCE: 73

Gly Val Gln Val Glu Thr Ile Ser Pro Gly Asp Gly Arg Thr Phe Pro
1               5                   10                  15

Lys Arg Gly Gln Thr Cys Val Val His Tyr Thr Gly Met Leu Glu Asp
            20                  25                  30

Gly Lys Lys Phe Asp Ser Ser Arg Asp Arg Asn Lys Pro Phe Lys Phe
        35                  40                  45

Met Leu Gly Lys Gln Glu Val Ile Arg Gly Trp Glu Glu Gly Val Ala
    50                  55                  60

Gln Met Ser Val Gly Gln Arg Ala Lys Leu Thr Ile Ser Pro Asp Tyr
65                  70                  75                  80

Ala Tyr Gly Ala Thr Gly His Pro Gly Ile Ile Pro Pro His Ala Thr
                85                  90                  95

Leu Val Phe Asp Val Glu Leu Leu Lys Leu Glu
            100                 105

<210> SEQ ID NO 74
<211> LENGTH: 342
<212> TYPE: PRT
<213> ORGANISM: Homo sapiens

<400> SEQUENCE: 74

Glu Asp Pro Ser Leu Asp Arg Pro Phe Ile Ser Glu Gly Thr Thr Leu
1               5                   10                  15

Lys Asp Leu Ile Tyr Asp Met Thr Thr Ser Gly Ser Gly Ser Gly Leu
            20                  25                  30

Pro Leu Leu Val Gln Arg Thr Ile Ala Arg Thr Ile Val Leu Gln Glu
        35                  40                  45

Ser Ile Gly Lys Gly Arg Phe Gly Glu Val Trp Arg Gly Lys Trp Arg
    50                  55                  60

Gly Glu Glu Val Ala Val Lys Ile Phe Ser Ser Arg Glu Glu Arg Ser
65                  70                  75                  80

```
Trp Phe Arg Glu Ala Glu Ile Tyr Gln Thr Val Met Leu Arg His Glu
                85                  90                  95

Asn Ile Leu Gly Phe Ile Ala Ala Asp Asn Lys Asp Asn Gly Thr Trp
            100                 105                 110

Thr Gln Leu Trp Leu Val Ser Asp Tyr His Glu His Gly Ser Leu Phe
        115                 120                 125

Asp Tyr Leu Asn Arg Tyr Thr Val Thr Val Glu Gly Met Ile Lys Leu
    130                 135                 140

Ala Leu Ser Thr Ala Ser Gly Leu Ala His Leu His Met Glu Ile Val
145                 150                 155                 160

Gly Thr Gln Gly Lys Pro Ala Ile Ala His Arg Asp Leu Lys Ser Lys
                165                 170                 175

Asn Ile Leu Val Lys Lys Asn Gly Thr Cys Cys Ile Ala Asp Leu Gly
            180                 185                 190

Leu Ala Val Arg His Asp Ser Ala Thr Asp Thr Ile Asp Ile Ala Pro
        195                 200                 205

Asn His Arg Val Gly Thr Lys Arg Tyr Met Ala Pro Glu Val Leu Asp
    210                 215                 220

Asp Ser Ile Asn Met Lys His Phe Glu Ser Phe Lys Arg Ala Asp Ile
225                 230                 235                 240

Tyr Ala Met Gly Leu Val Phe Trp Glu Ile Ala Arg Arg Cys Ser Ile
                245                 250                 255

Gly Gly Ile His Glu Asp Tyr Gln Leu Pro Tyr Tyr Asp Leu Val Pro
            260                 265                 270

Ser Asp Pro Ser Val Glu Glu Met Arg Lys Val Val Cys Glu Gln Lys
        275                 280                 285

Leu Arg Pro Asn Ile Pro Asn Arg Trp Gln Ser Cys Glu Ala Leu Arg
    290                 295                 300

Val Met Ala Lys Ile Met Arg Glu Cys Trp Tyr Ala Asn Gly Ala Ala
305                 310                 315                 320

Arg Leu Thr Ala Leu Arg Ile Lys Lys Thr Leu Ser Gln Leu Ser Gln
                325                 330                 335

Gln Glu Gly Ile Lys Met
            340

<210> SEQ ID NO 75
<211> LENGTH: 785
<212> TYPE: PRT
<213> ORGANISM: Homo sapiens

<400> SEQUENCE: 75

Met Thr Ser His Tyr Val Ile Ala Ile Phe Ala Leu Met Ser Ser Cys
1               5                   10                  15

Leu Ala Thr Ala Gly Pro Glu Pro Gly Ala Leu Cys Glu Leu Ser Pro
            20                  25                  30

Val Ser Ala Ser His Pro Val Gln Ala Leu Met Glu Ser Phe Thr Val
        35                  40                  45

Leu Ser Gly Cys Ala Ser Arg Gly Thr Thr Gly Leu Pro Gln Glu Val
    50                  55                  60

His Val Leu Asn Leu Arg Thr Ala Gly Gln Gly Pro Gly Gln Leu Gln
65                  70                  75                  80

Arg Glu Val Thr Leu His Leu Asn Pro Ile Ser Ser Val His Ile His
                85                  90                  95

His Lys Ser Val Val Phe Leu Leu Asn Ser Pro His Pro Leu Val Trp
            100                 105                 110
```

-continued

```
His Leu Lys Thr Glu Arg Leu Ala Thr Gly Val Ser Arg Leu Phe Leu
            115                 120                 125

Val Ser Glu Gly Ser Val Val Gln Phe Ser Ser Ala Asn Phe Ser Leu
        130                 135                 140

Thr Ala Glu Thr Glu Glu Arg Asn Phe Pro His Gly Asn Glu His Leu
145                 150                 155                 160

Leu Asn Trp Ala Arg Lys Glu Tyr Gly Ala Val Thr Ser Phe Thr Glu
                165                 170                 175

Leu Lys Ile Ala Arg Asn Ile Tyr Ile Lys Val Gly Glu Asp Gln Val
            180                 185                 190

Phe Pro Pro Lys Cys Asn Ile Gly Lys Asn Phe Leu Ser Leu Asn Tyr
        195                 200                 205

Leu Ala Glu Tyr Leu Gln Pro Lys Ala Ala Glu Gly Cys Val Met Ser
    210                 215                 220

Ser Gln Pro Gln Asn Glu Glu Val His Ile Ile Glu Leu Ile Thr Pro
225                 230                 235                 240

Asn Ser Asn Pro Tyr Ser Ala Phe Gln Val Asp Ile Thr Ile Asp Ile
                245                 250                 255

Arg Pro Ser Gln Glu Asp Leu Glu Val Val Lys Asn Leu Ile Leu Ile
            260                 265                 270

Leu Lys Cys Lys Lys Ser Val Asn Trp Val Ile Lys Ser Phe Asp Val
        275                 280                 285

Lys Gly Ser Leu Lys Ile Ile Ala Pro Asn Ser Ile Gly Phe Gly Lys
    290                 295                 300

Glu Ser Glu Arg Ser Met Thr Met Thr Lys Ser Ile Arg Asp Asp Ile
305                 310                 315                 320

Pro Ser Thr Gln Gly Asn Leu Val Lys Trp Ala Leu Asp Asn Gly Tyr
                325                 330                 335

Ser Pro Ile Thr Ser Tyr Thr Met Ala Pro Val Ala Asn Arg Phe His
            340                 345                 350

Leu Arg Leu Glu Asn Asn Glu Glu Met Gly Asp Glu Glu Val His Thr
        355                 360                 365

Ile Pro Pro Glu Leu Arg Ile Leu Leu Asp Pro Gly Ala Leu Pro Ala
    370                 375                 380

Leu Gln Asn Pro Pro Ile Arg Gly Gly Glu Gly Gln Asn Gly Gly Leu
385                 390                 395                 400

Pro Phe Pro Phe Pro Asp Ile Ser Arg Arg Val Trp Asn Glu Glu Gly
                405                 410                 415

Glu Asp Gly Leu Pro Arg Pro Lys Asp Pro Val Ile Pro Ser Ile Gln
            420                 425                 430

Leu Phe Pro Gly Leu Arg Glu Pro Glu Glu Val Gln Gly Ser Val Asp
        435                 440                 445

Ile Ala Leu Ser Val Lys Cys Asp Asn Glu Lys Met Ile Val Ala Val
    450                 455                 460

Glu Lys Asp Ser Phe Gln Ala Ser Gly Tyr Ser Gly Met Asp Val Thr
465                 470                 475                 480

Leu Leu Asp Pro Thr Cys Lys Ala Lys Met Asn Gly Thr His Phe Val
                485                 490                 495

Leu Glu Ser Pro Leu Asn Gly Cys Gly Thr Arg Pro Arg Trp Ser Ala
            500                 505                 510

Leu Asp Gly Val Val Tyr Tyr Asn Ser Ile Val Ile Gln Val Pro Ala
        515                 520                 525
```

```
Leu Gly Asp Ser Ser Gly Trp Pro Asp Gly Tyr Glu Asp Leu Glu Ser
    530                 535                 540

Gly Asp Asn Gly Phe Pro Gly Asp Met Asp Glu Gly Asp Ala Ser Leu
545                 550                 555                 560

Phe Thr Arg Pro Glu Ile Val Val Phe Asn Cys Ser Leu Gln Gln Val
                565                 570                 575

Arg Asn Pro Ser Ser Phe Gln Glu Gln Pro His Gly Asn Ile Thr Phe
            580                 585                 590

Asn Met Glu Leu Tyr Asn Thr Asp Leu Phe Leu Val Pro Ser Gln Gly
        595                 600                 605

Val Phe Ser Val Pro Glu Asn Gly His Val Tyr Val Glu Val Ser Val
    610                 615                 620

Thr Lys Ala Glu Gln Glu Leu Gly Phe Ala Ile Gln Thr Cys Phe Ile
625                 630                 635                 640

Ser Pro Tyr Ser Asn Pro Asp Arg Met Ser His Tyr Thr Ile Ile Glu
                645                 650                 655

Asn Ile Cys Pro Lys Asp Glu Ser Val Lys Phe Tyr Ser Pro Lys Arg
            660                 665                 670

Val His Phe Pro Ile Pro Gln Ala Asp Met Asp Lys Lys Arg Phe Ser
        675                 680                 685

Phe Val Phe Lys Pro Val Phe Asn Thr Ser Leu Leu Phe Leu Gln Cys
    690                 695                 700

Glu Leu Thr Leu Cys Thr Lys Met Glu Lys His Pro Gln Lys Leu Pro
705                 710                 715                 720

Lys Cys Val Pro Pro Asp Glu Ala Cys Thr Ser Leu Asp Ala Ser Ile
                725                 730                 735

Ile Trp Ala Met Met Gln Asn Lys Lys Thr Phe Thr Lys Pro Leu Ala
            740                 745                 750

Val Ile His His Glu Ala Glu Ser Lys Glu Lys Gly Pro Ser Met Lys
        755                 760                 765

Glu Pro Asn Pro Ile Ser Pro Pro Ile Phe His Gly Leu Asp Thr Leu
    770                 775                 780

Thr
785

<210> SEQ ID NO 76
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 76
aagcttgccg ccgccatggg tcg                                            23

<210> SEQ ID NO 77
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 77
ctggaattcg tcaggattgc tgg                                            23

<210> SEQ ID NO 78
```

-continued

```
<211> LENGTH: 477
<212> TYPE: PRT
<213> ORGANISM: Homo sapiens

<400> SEQUENCE: 78

Met Gly Arg Gly Leu Leu Arg Gly Leu Trp Pro Leu His Ile Val Leu
1               5                   10                  15

Trp Thr Arg Ile Ala Ser Thr Ile Pro Pro His Val Gln Lys Ser Val
            20                  25                  30

Asn Asn Asp Met Ile Val Thr Asp Asn Asn Gly Ala Val Lys Phe Pro
        35                  40                  45

Gln Leu Cys Lys Phe Cys Asp Val Arg Phe Ser Thr Cys Asp Asn Gln
    50                  55                  60

Lys Ser Cys Met Ser Asn Cys Ser Ile Thr Ser Ile Cys Glu Lys Pro
65                  70                  75                  80

Gln Glu Val Cys Val Ala Val Trp Arg Lys Asn Asp Glu Asn Ile Thr
                85                  90                  95

Leu Glu Thr Val Cys His Asp Pro Lys Leu Pro Tyr His Asp Phe Ile
            100                 105                 110

Leu Glu Asp Ala Ala Ser Pro Lys Cys Ile Met Lys Glu Lys Lys Lys
        115                 120                 125

Pro Gly Glu Thr Phe Phe Met Cys Ser Cys Ser Ser Asp Glu Cys Asn
    130                 135                 140

Asp Asn Ile Ile Phe Ser Glu Glu Tyr Asn Thr Ser Asn Pro Asp Leu
145                 150                 155                 160

Leu Leu Val Ile Phe Gln Val Thr Gly Ile Ser Leu Leu Pro Pro Leu
                165                 170                 175

Gly Val Ala Ile Ser Val Ile Ile Ile Phe Tyr Cys Tyr Arg Val Asn
            180                 185                 190

Arg Gln Gln Lys Leu Ser Ser Thr Trp Glu Thr Gly Lys Thr Arg Lys
        195                 200                 205

Leu Met Glu Phe Ser Glu His Cys Ala Ile Ile Leu Glu Asp Asp Arg
    210                 215                 220

Ser Asp Ile Ser Ser Thr Cys Ala Asn Asn Ile Asn His Asn Thr Glu
225                 230                 235                 240

Leu Leu Pro Ile Glu Leu Asp Thr Leu Val Gly Lys Gly Arg Phe Ala
                245                 250                 255

Glu Val Tyr Lys Ala Lys Leu Lys Gln Asn Thr Ser Glu Gln Phe Glu
            260                 265                 270

Thr Val Ala Val Lys Ile Phe Pro Tyr Glu Glu Tyr Ala Ser Trp Lys
        275                 280                 285

Thr Glu Lys Asp Ile Phe Ser Asp Ile Asn Leu Lys His Glu Asn Ile
    290                 295                 300

Leu Gln Phe Leu Thr Ala Glu Glu Arg Lys Thr Glu Leu Gly Lys Gln
305                 310                 315                 320

Tyr Trp Leu Ile Thr Ala Phe His Ala Lys Gly Asn Leu Gln Glu Tyr
                325                 330                 335

Leu Thr Arg His Val Ile Ser Trp Glu Asp Leu Arg Lys Leu Gly Ser
            340                 345                 350

Ser Leu Ala Arg Gly Ile Ala His Leu His Ser Asp His Thr Pro Cys
        355                 360                 365

Gly Arg Pro Lys Met Pro Ile Val His Arg Asp Leu Lys Ser Ser Asn
    370                 375                 380

Ile Leu Val Lys Asn Asp Leu Thr Cys Cys Leu Cys Asp Phe Gly Leu
```

```
385                 390                 395                 400
Ser Leu Arg Leu Asp Pro Thr Leu Ser Val Asp Asp Leu Ala Asn Ser
            405                 410                 415

Gly Gln Val Gly Thr Ala Arg Tyr Met Ala Pro Glu Val Leu Glu Ser
            420                 425                 430

Arg Met Asn Leu Glu Asn Val Glu Ser Phe Lys Gln Thr Asp Val Tyr
            435                 440                 445

Ser Met Ala Leu Val Leu Trp Glu Met Thr Ser Arg Cys Asn Ala Val
        450                 455                 460

Gly Glu Val Lys Asp Tyr Glu Pro Pro Phe Gly Ser Lys
465                 470                 475

<210> SEQ ID NO 79
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 79

Thr Gly Gly Gly
1
```